(12) United States Patent
Hermez et al.

(10) Patent No.: US 11,278,689 B2
(45) Date of Patent: Mar. 22, 2022

(54) HUMIDIFICATION OF RESPIRATORY GASES

(71) Applicant: Fisher & Paykel Healthcare Limited, Auckland (NZ)

(72) Inventors: Laith Adeeb Hermez, Auckland (NZ); Stephen David Evans, Auckland (NZ); Hamish Osborne, Auckland (NZ); Michael John Andresen, Auckland (NZ); Anthony James Newland, Auckland (NZ); Dexter Chi Lun Cheung, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 487 days.

(21) Appl. No.: 15/525,257

(22) PCT Filed: Nov. 17, 2015

(86) PCT No.: PCT/NZ2015/050193
§ 371 (c)(1),
(2) Date: May 8, 2017

(87) PCT Pub. No.: WO2016/080847
PCT Pub. Date: May 26, 2016

(65) Prior Publication Data
US 2018/0280644 A1  Oct. 4, 2018

Related U.S. Application Data

(60) Provisional application No. 62/080,814, filed on Nov. 17, 2014.

(51) Int. Cl.
*A61M 16/00* (2006.01)
*A61M 16/10* (2006.01)
*A61M 16/16* (2006.01)

(52) U.S. Cl.
CPC ...... *A61M 16/024* (2017.08); *A61M 16/0003* (2014.02); *A61M 16/109* (2014.02);
(Continued)

(58) Field of Classification Search
CPC ............ A61M 16/0003; A61M 16/024; A61M 16/109; A61M 16/161; A61M 2016/0033;
(Continued)

(56) References Cited

U.S. PATENT DOCUMENTS 1,154,259 A  9/1915 Light
2,634,311 A  4/1953 Darling
(Continued)

FOREIGN PATENT DOCUMENTS

AU  2002244571  10/2002
AU  2007317198  8/2013
(Continued)

OTHER PUBLICATIONS

International Preliminary Report on Patentability in PCT/NZ2015/050193 dated Jun. 1, 2017 in 2 pages.
(Continued)

*Primary Examiner* — Elliot S Ruddie
(74) *Attorney, Agent, or Firm* — Knobbe Martens Olson & Bear, LLP

(57) ABSTRACT

A system for humidifying respiratory gases has a humidification apparatus, a humidification chamber, a heating apparatus and a sensor. The sensor is configured to determine a characteristic of the gases flow and communicate this to a controller which controls the power supplied to the heating apparatus with respect to information regarding the characteristic of the gases flow. A structure partially encloses the humidification chamber and allows energy loss through a
(Continued)

wall of the humidification chamber. The humidification chamber may have features to promote heat loss through the wall of the chamber.

13 Claims, 17 Drawing Sheets

(52) U.S. Cl.
CPC .......... *A61M 16/16* (2013.01); *A61M 16/161* (2014.02); *A61M 2016/003* (2013.01); *A61M 2016/0033* (2013.01); *A61M 2205/02* (2013.01); *A61M 2205/0244* (2013.01); *A61M 2205/3334* (2013.01); *A61M 2205/3368* (2013.01); *A61M 2205/362* (2013.01); *A61M 2205/3606* (2013.01); *A61M 2205/502* (2013.01)

(58) Field of Classification Search
CPC ...... A61M 2205/02; A61M 2205/0244; A61M 2205/3334; A61M 2205/3606; A61M 2205/362; A61M 2205/502; A61M 16/022–024; A61M 16/16–168; A61M 2016/003–0042; A61M 16/1075–1095; A61M 2205/3368–3372; A61M 2205/36–362
USPC .................................................. 128/203.14
See application file for complete search history.

(56) References Cited

U.S. PATENT DOCUMENTS

| | | |
|---|---|---|
| 2,745,074 A | 5/1956 | Darling |
| 3,163,707 A | 12/1964 | Darling |
| 3,283,580 A | 11/1966 | Nanigian et al. |
| 3,394,954 A | 7/1968 | Sarns |
| 3,485,237 A | 12/1969 | Bedford |
| 3,582,094 A | 6/1971 | Whittaker |
| 3,588,859 A | 6/1971 | Petree |
| 3,638,926 A | 2/1972 | Melville et al. |
| 3,659,604 A | 5/1972 | Melville et al. |
| 3,703,892 A | 11/1972 | Meyers |
| 3,777,298 A | 12/1973 | Newman |
| 3,903,742 A | 9/1975 | Colton |
| 3,954,920 A | 5/1976 | Heath |
| 3,987,133 A | 10/1976 | Andra |
| 3,990,727 A | 11/1976 | Gallagher |
| 4,028,444 A | 6/1977 | Brown et al. |
| 4,038,519 A | 7/1977 | Foucras |
| 4,060,576 A | 11/1977 | Grant |
| 4,111,197 A | 9/1978 | Warncke et al. |
| 4,139,762 A | 2/1979 | Pohrer et al. |
| 4,172,709 A | 10/1979 | Keppel et al. |
| 4,183,248 A | 1/1980 | West |
| 4,269,573 A * | 5/1981 | Goode ...................... F28D 5/02 261/29 |
| 4,333,451 A | 6/1982 | Paluch |
| 4,473,923 A | 10/1984 | Neroni et al. |
| 4,529,867 A | 7/1985 | Velnosky et al. |
| 4,545,290 A | 10/1985 | Lieberman |
| 4,564,748 A | 1/1986 | Gupton |
| 4,588,425 A | 5/1986 | Usry et al. |
| 4,621,632 A | 11/1986 | Bartels et al. |
| 4,676,237 A | 6/1987 | Wood et al. |
| 4,686,354 A | 8/1987 | Makin |
| 4,708,831 A | 11/1987 | Elsworth et al. |
| 4,774,032 A | 9/1988 | Coates et al. |
| 4,813,280 A | 3/1989 | Miller et al. |
| 4,844,512 A | 7/1989 | Gahwiler |
| 4,942,877 A | 7/1990 | Sakai et al. |
| 4,944,310 A | 7/1990 | Sullivan |
| 4,967,744 A | 11/1990 | Chua |
| 5,031,612 A | 7/1991 | Clementi |
| 5,058,588 A | 10/1991 | Kaestle |
| 5,060,506 A | 10/1991 | Douglas |
| 5,117,819 A | 6/1992 | Servidio et al. |
| 5,134,996 A | 8/1992 | Bell |
| 5,148,801 A | 9/1992 | Douwens et al. |
| 5,213,376 A | 5/1993 | Szabo |
| RE34,599 E | 5/1994 | Suszynski et al. |
| 5,357,948 A | 10/1994 | Eilentropp |
| 5,367,604 A | 11/1994 | Murray |
| 5,392,770 A | 2/1995 | Clawson et al. |
| 5,454,061 A | 9/1995 | Carlson |
| 5,483,616 A | 1/1996 | Chiu et al. |
| 5,537,996 A | 7/1996 | McPhee |
| 5,551,883 A | 9/1996 | Davis |
| 5,640,951 A | 6/1997 | Huddart et al. |
| 5,660,567 A | 8/1997 | Nierlich et al. |
| 5,720,293 A | 2/1998 | Quinn et al. |
| 5,778,872 A | 7/1998 | Fukunaga et al. |
| 5,906,201 A | 5/1999 | Nilson |
| 5,943,473 A | 8/1999 | Levine |
| D419,522 S | 1/2000 | Kamagai |
| 6,039,696 A | 3/2000 | Bell |
| 6,053,482 A | 4/2000 | Glenn et al. |
| 6,078,729 A | 6/2000 | Kopel |
| 6,090,036 A * | 7/2000 | Kobayashi ............. A61G 11/00 600/22 |
| 6,102,037 A | 8/2000 | Koch |
| 6,105,970 A | 8/2000 | Siegrist et al. |
| 6,126,610 A | 10/2000 | Rich et al. |
| 6,138,674 A | 10/2000 | Gull et al. |
| 6,196,980 B1 | 3/2001 | Akerfeldt et al. |
| 6,201,983 B1 | 3/2001 | Haumann et al. |
| 6,226,451 B1 | 5/2001 | Wong |
| 6,349,722 B1 | 2/2002 | Gradon et al. |
| 6,360,741 B2 | 3/2002 | Truschel |
| 6,402,207 B1 | 6/2002 | Segal et al. |
| 6,435,180 B1 * | 8/2002 | Hewson ................ A61M 16/16 128/203.12 |
| 6,467,477 B1 | 10/2002 | Frank et al. |
| 6,508,249 B2 | 1/2003 | Hoenig |
| 6,511,075 B1 | 1/2003 | Schmidt |
| 6,551,143 B2 | 4/2003 | Tanaka et al. |
| 6,554,260 B1 | 4/2003 | Lipscombe et al. |
| 6,591,061 B2 | 7/2003 | Wang |
| 6,598,604 B1 | 7/2003 | Seakins |
| 6,612,624 B1 | 9/2003 | Seagal et al. |
| 6,648,669 B1 | 11/2003 | Kim et al. |
| 6,668,828 B1 | 12/2003 | Figley et al. |
| 6,685,491 B2 | 2/2004 | Gergek |
| 6,827,084 B2 | 12/2004 | Grubb, Jr. et al. |
| 6,874,771 B2 | 4/2005 | Birdsell et al. |
| 6,895,803 B2 | 5/2005 | Seakins et al. |
| 6,918,389 B2 | 7/2005 | Seakins et al. |
| 6,935,337 B2 | 8/2005 | Virr et al. |
| 6,943,566 B2 | 9/2005 | Florin et al. |
| 6,953,354 B2 | 10/2005 | Edirisuriya et al. |
| 7,043,979 B2 | 5/2006 | Smith et al. |
| 7,063,668 B2 | 6/2006 | Cardelius et al. |
| 7,086,422 B2 | 8/2006 | Huber et al. |
| 7,090,541 B1 | 8/2006 | Ho |
| 7,096,864 B1 | 8/2006 | Mayer et al. |
| 7,120,354 B2 | 10/2006 | Mackie et al. |
| 7,137,654 B2 | 11/2006 | Segal et al. |
| 7,140,367 B2 | 11/2006 | White et al. |
| 7,157,035 B2 | 1/2007 | Edirisuriya et al. |
| 7,191,780 B2 | 3/2007 | Faram |
| 7,225,809 B1 | 6/2007 | Bowen et al. |
| 7,284,554 B2 | 10/2007 | Shaw |
| 7,327,547 B1 | 2/2008 | Epstein |
| 7,327,949 B1 | 2/2008 | Cheng et al. |
| 7,334,587 B2 | 2/2008 | Lake |
| 7,364,436 B2 | 4/2008 | Yen |
| 7,396,995 B2 | 7/2008 | Laurent et al. |
| 7,448,383 B2 | 11/2008 | Delache et al. |
| 7,478,635 B2 | 1/2009 | Wixey et al. |
| 7,525,663 B2 | 4/2009 | Kwok et al. |
| 7,637,288 B2 | 12/2009 | Kressierer/Huber et al. |
| 7,677,246 B2 | 3/2010 | Kepler et al. |
| 7,766,050 B2 | 8/2010 | Patel |

(56) References Cited

U.S. PATENT DOCUMENTS

| | | |
|---|---|---|
| 7,794,426 B2 | 9/2010 | Briones et al. |
| 7,814,907 B2 | 10/2010 | Bremner et al. |
| D628,288 S | 11/2010 | Row et al. |
| 7,827,981 B2 | 11/2010 | Bamford |
| 7,870,857 B2 | 1/2011 | Dhuper et al. |
| 7,913,689 B2 | 3/2011 | Henry et al. |
| 7,942,380 B2 | 5/2011 | Bertinetti et al. |
| 7,942,389 B2 | 5/2011 | Koch et al. |
| 7,965,930 B2 | 6/2011 | Carlson et al. |
| 7,983,542 B2 | 7/2011 | McGhin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,059,947 B2 | 11/2011 | Bradley et al. |
| 8,063,343 B2 | 11/2011 | McGhin et al. |
| 8,078,040 B2 | 12/2011 | Forrester |
| 8,100,124 B2 | 1/2012 | Becker et al. |
| 8,122,882 B2 | 2/2012 | McGhin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Payton et al. |
| 8,197,123 B2 | 6/2012 | Snyder et al. |
| 8,221,530 B2 | 7/2012 | Peter et al. |
| 8,245,709 B2 | 8/2012 | Rossen et al. |
| 8,245,710 B2 | 8/2012 | Makinson et al. |
| 8,253,076 B2 | 8/2012 | Andel et al. |
| 8,257,286 B2 | 9/2012 | Meyer et al. |
| 8,267,084 B2 | 9/2012 | Kwok |
| 8,287,517 B2 | 10/2012 | Ito |
| 8,316,848 B2 | 11/2012 | Kwok et al. |
| 8,333,194 B2 | 12/2012 | Lewis et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,469,025 B2 | 6/2013 | Mayer et al. |
| 8,490,621 B2 | 7/2013 | Radomski et al. |
| 8,496,001 B2 | 7/2013 | Schermeier et al. |
| RE44,453 E | 8/2013 | Virr et al. |
| 8,511,305 B2 | 8/2013 | Liu et al. |
| 8,511,651 B2 | 8/2013 | Fridberg et al. |
| 8,522,782 B2 | 9/2013 | Lewis et al. |
| 8,528,552 B2 | 9/2013 | von Blumenthal |
| 8,544,465 B2 | 10/2013 | Smith et al. |
| 8,550,072 B2 | 10/2013 | Thudor et al. |
| 8,631,789 B2 | 1/2014 | Virr et al. |
| 8,640,696 B2 | 2/2014 | Pujol et al. |
| 8,733,348 B2 | 5/2014 | Korneff et al. |
| 8,733,349 B2 | 5/2014 | Bath et al. |
| 8,770,190 B2 | 7/2014 | Doherty et al. |
| 8,800,970 B2 | 8/2014 | Heine et al. |
| 8,844,521 B2 | 9/2014 | McCarthy |
| 8,851,071 B2 | 10/2014 | Kuo et al. |
| 8,905,023 B2 | 12/2014 | Niland et al. |
| 8,915,250 B2 | 12/2014 | Dugan et al. |
| 8,931,481 B2 | 1/2015 | Jones et al. |
| 8,939,147 B2 | 1/2015 | Henry et al. |
| 8,985,105 B2 | 3/2015 | Burton et al. |
| 9,022,946 B2 | 5/2015 | Haque |
| 9,067,036 B2 | 6/2015 | Korneff et al. |
| 9,119,933 B2 | 9/2015 | Bedford et al. |
| 9,132,252 B2 | 9/2015 | Barlow et al. |
| 9,162,035 B2 | 10/2015 | Kwok |
| 9,186,477 B2 | 11/2015 | Hunt et al. |
| 9,205,220 B2 | 12/2015 | Korneff et al. |
| 9,212,673 B2 | 12/2015 | Korneff et al. |
| 9,242,064 B2 | 1/2016 | Rustad et al. |
| 9,254,368 B2 | 2/2016 | von Blumenthal et al. |
| 9,289,572 B2 | 3/2016 | Korneff et al. |
| RE46,079 E | 7/2016 | Virr et al. |
| 9,381,317 B2 | 7/2016 | Landis et al. |
| 9,387,299 B2 | 7/2016 | Zwolinsky et al. |
| 9,427,547 B2 | 8/2016 | Landis et al. |
| 9,446,210 B2 | 9/2016 | Orr et al. |
| 9,517,321 B2 | 12/2016 | Buechi et al. |
| 9,545,493 B2 | 1/2017 | Mayer et al. |
| 9,566,409 B2 | 2/2017 | Grundler et al. |
| 9,572,949 B2 | 2/2017 | Vos et al. |
| 9,572,951 B2 | 2/2017 | Barket et al. |
| 9,586,019 B2 | 3/2017 | Heine et al. |
| 9,642,979 B2 | 5/2017 | Korneff et al. |
| 9,838,759 B2 | 12/2017 | Kirmse et al. |
| 9,861,778 B2 | 1/2018 | Bath et al. |
| 9,937,314 B2 | 4/2018 | Buechi et al. |
| 9,937,316 B2 | 4/2018 | Buechi et al. |
| 10,046,136 B2 | 8/2018 | Pujol |
| 2001/0017134 A1 | 8/2001 | Bahr |
| 2001/0050080 A1 | 12/2001 | Seakins et al. |
| 2002/0100320 A1 | 8/2002 | Smith et al. |
| 2003/0148664 A1 | 8/2003 | Cheng |
| 2003/0200727 A1 | 10/2003 | Kim |
| 2003/0236015 A1 | 12/2003 | Edirisuriya et al. |
| 2004/0074493 A1 | 4/2004 | Seakins et al. |
| 2004/0087213 A1 | 5/2004 | Kao |
| 2004/0149284 A1 | 8/2004 | Smith et al. |
| 2004/0221843 A1 | 11/2004 | Baecke |
| 2004/0234254 A1* | 11/2004 | Czupich ............... A61G 11/00 392/403 |
| 2004/0239001 A1 | 12/2004 | Edirisuriya et al. |
| 2004/0244858 A1 | 12/2004 | Jeong |
| 2006/0030191 A1 | 2/2006 | Tuin et al. |
| 2006/0118113 A1 | 6/2006 | Bremner et al. |
| 2006/0137445 A1 | 6/2006 | Smith et al. |
| 2006/0237012 A1 | 10/2006 | Thudor et al. |
| 2007/0039374 A1 | 2/2007 | Borali |
| 2007/0079982 A1 | 4/2007 | Laurent et al. |
| 2007/0107737 A1 | 5/2007 | Landis et al. |
| 2007/0144519 A1 | 6/2007 | Henry et al. |
| 2007/0163295 A1* | 7/2007 | Martin ..................... F24F 1/08 62/507 |
| 2007/0175473 A1 | 8/2007 | Lewis et al. |
| 2007/0248934 A1 | 10/2007 | Mosimann |
| 2007/0284361 A1 | 12/2007 | Nadjafizadeh et al. |
| 2008/0000474 A1 | 1/2008 | Jochle et al. |
| 2008/0015257 A1 | 1/2008 | Grosskreutz et al. |
| 2008/0051674 A1 | 2/2008 | Davenport et al. |
| 2008/0066751 A1 | 3/2008 | Polacsek |
| 2008/0105257 A1 | 5/2008 | Klasek et al. |
| 2008/0142019 A1 | 6/2008 | Lewis et al. |
| 2008/0202512 A1 | 8/2008 | Kressierer et al. |
| 2008/0251073 A1 | 10/2008 | Jassell et al. |
| 2009/0050150 A1 | 2/2009 | Rossen et al. |
| 2009/0107493 A1 | 4/2009 | Liu et al. |
| 2009/0107496 A1 | 4/2009 | McGhin et al. |
| 2009/0107501 A1 | 4/2009 | Krieger |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0174092 A1 | 7/2009 | Kwok et al. |
| 2009/0223514 A1 | 9/2009 | Smith et al. |
| 2009/0301482 A1 | 12/2009 | Burton et al. |
| 2009/0320840 A1 | 12/2009 | Klasek et al. |
| 2010/0043791 A1 | 2/2010 | McAuley et al. |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0242963 A1 | 9/2010 | Brieger et al. |
| 2010/0307495 A1 | 12/2010 | Kepler et al. |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0088693 A1 | 4/2011 | Somervell et al. |
| 2011/0108031 A1 | 5/2011 | Stauber |
| 2011/0114093 A1 | 5/2011 | Patil et al. |
| 2011/0155132 A1 | 6/2011 | Virr et al. |

(56) References Cited

U.S. PATENT DOCUMENTS

| | | |
|---|---|---|
| 2011/0162649 A1* | 7/2011 | Potharaju .......... A61M 16/0066 128/203.26 |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0288474 A1 | 11/2011 | Ott et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0037156 A9 | 2/2012 | Tatkov et al. |
| 2012/0060838 A1 | 3/2012 | Laura Lapoint et al. |
| 2012/0125333 A1 | 5/2012 | Bedford et al. |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0255758 A1 | 10/2012 | Lee |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112202 A1 | 5/2013 | Fogelbrink |
| 2013/0174839 A1 | 7/2013 | Ging et al. |
| 2013/0206140 A1 | 8/2013 | Kepler et al. |
| 2013/0239966 A1 | 9/2013 | Klasek et al. |
| 2013/0247905 A1 | 9/2013 | Miller et al. |
| 2013/0255677 A1 | 10/2013 | Varga |
| 2013/0333701 A1 | 12/2013 | Herron |
| 2013/0340752 A1 | 12/2013 | Landis et al. |
| 2014/0020684 A1 | 1/2014 | Klasek et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0216446 A1 | 7/2014 | Wruck |
| 2014/0216459 A1* | 8/2014 | Vos .................. A61M 16/1095 128/204.17 |
| 2014/0251322 A1 | 9/2014 | Miller et al. |
| 2014/0311489 A1 | 10/2014 | Heine et al. |
| 2014/0318536 A1 | 10/2014 | Landis et al. |
| 2014/0251331 A1 | 11/2014 | Korneff et al. |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0040897 A1 | 2/2015 | Beuechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |
| 2016/0008560 A1 | 1/2016 | Kwok |
| 2016/0015927 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0367776 A1 | 12/2016 | Landis et al. |
| 2016/0367779 A1 | 12/2016 | Landis et al. |
| 2017/0095635 A1 | 4/2017 | Huby et al. |
| 2017/0136198 A1 | 5/2017 | Delangre et al. |
| 2017/0161461 A1 | 6/2017 | Delanger et al. |
| 2017/0173293 A1 | 6/2017 | Osborne et al. |
| 2017/0239432 A1 | 8/2017 | Delanger et al. |
| 2017/0326320 A1 | 11/2017 | Baigent et al. |
| 2018/0078730 A1 | 3/2018 | Bath et al. |
| 2018/0169361 A1 | 6/2018 | Dennis et al. |
| 2018/0250491 A1 | 9/2018 | Row et al. |

FOREIGN PATENT DOCUMENTS

| | | | |
|---|---|---|---|
| AU | 2010206053 | 8/2014 | |
| CA | 2495451 | 8/2011 | |
| CA | 2867266 A1 * | 9/2013 | ........ A61M 16/0816 |
| CN | 1598510 | 3/2005 | |
| DE | 3110903 | 9/1982 | |
| DE | 3618614 | 12/1987 | |
| DE | 4102223 | 7/1992 | |
| DE | 4020522 | 9/1993 | |
| DE | 19647548 | 5/1999 | |
| DE | 19958296 | 9/2001 | |
| DE | 202004006484 | 9/2005 | |
| DE | 102004030747 | 1/2006 | |
| DE | 202005008152 | 10/2006 | |
| DE | 202005008156 | 10/2006 | |
| DE | 20321468 | 8/2007 | |
| DE | 20321469 | 8/2007 | |
| DE | 20321470 | 8/2007 | |
| DE | 20321471 | 8/2007 | |
| DE | 20321472 | 8/2007 | |
| DE | 202006007397 | 9/2007 | |
| DE | 202006011754 | 12/2007 | |
| DE | 20122844 | 5/2008 | |
| DE | 102007003455 | 3/2009 | |
| DE | 102007003454 | 5/2009 | |
| DE | 102008001022 | 10/2009 | |
| DE | 20122937 | 9/2010 | |
| DE | 202004021757 | 9/2010 | |
| DE | 202004021758 | 9/2010 | |
| DE | 202004021756 | 10/2010 | |
| DE | 202004021759 | 10/2010 | |
| DE | 202004021774 | 11/2010 | |
| DE | 202004021777 | 12/2010 | |
| DE | 202004021794 | 2/2011 | |
| DE | 202004021795 | 2/2011 | |
| DE | 202004021796 | 2/2011 | |
| DE | 202004021798 | 2/2011 | |
| DE | 202006020951 | 2/2011 | |
| DE | 202006020952 | 2/2011 | |
| DE | 20122943 | 5/2011 | |
| DE | 20122944 | 5/2011 | |
| DE | 20122945 | 5/2011 | |
| DE | 202004021829 | 5/2011 | |
| DE | 202005021927 | 6/2011 | |
| DE | 202006021019 | 11/2011 | |
| DE | 20321882 | 12/2011 | |
| DE | 202004021876 | 1/2012 | |
| DE | 202007019350 | 1/2012 | |
| DE | 202011107902 | 1/2012 | |
| DE | 202010016037 | 3/2012 | |
| DE | 202012007229 | 10/2012 | |
| DE | 102007039391 | 6/2016 | |
| EP | 0201985 | 11/1986 | |
| EP | 0291921 | 10/1991 | |
| EP | 0567158 | 10/1993 | |
| EP | 0535952 | 12/1997 | |
| EP | 1262208 | 12/2002 | |
| EP | 1352670 | 10/2003 | |
| EP | 0885623 | 11/2004 | |
| EP | 1741462 | 11/2007 | |
| EP | 2236167 | 10/2011 | |
| EP | 2415445 | 2/2012 | |
| EP | 2471568 | 7/2012 | |
| EP | 2340867 | 5/2013 | |
| EP | 2514478 | 7/2013 | |
| EP | 2703034 A2 | 3/2014 | |
| EP | 2089086 | 5/2014 | |
| EP | 1646910 | 8/2015 | |
| EP | 1924311 | 9/2015 | |
| EP | 3053623 | 8/2016 | |
| EP | 2355881 | 12/2016 | |
| EP | 2335761 | 4/2017 | |
| EP | 1669098 | 10/2017 | |
| EP | 2307082 | 4/2018 | |

(56) References Cited

FOREIGN PATENT DOCUMENTS

| | | |
|---|---|---|
| EP | 2195061 | 8/2018 |
| GB | 1310949 | 3/1973 |
| GB | 1364127 | 8/1974 |
| GB | 2176313 | 12/1986 |
| JP | 03194747 | 8/1991 |
| JP | H0623051 | 2/1994 |
| JP | 11248076 | 9/1999 |
| JP | 2001095920 | 4/2001 |
| JP | 2003275312 | 9/2003 |
| JP | 4242816 | 3/2009 |
| NZ | 564886 | 2/2011 |
| NZ | 586325 | 1/2012 |
| NZ | 597020 | 6/2013 |
| NZ | 604137 | 6/2014 |
| NZ | 625605 | 4/2016 |
| NZ | 710078 | 1/2017 |
| NZ | 710078 A | 1/2017 |
| NZ | 631008 | 7/2017 |
| WO | WO 1997/18001 A1 | 5/1997 |
| WO | WO 2000/029057 A1 | 5/2000 |
| WO | WO 2001/032069 A2 | 5/2001 |
| WO | WO 2001/097894 A1 | 12/2001 |
| WO | WO 2002/066106 A1 | 8/2002 |
| WO | WO 2002/066107 A1 | 8/2002 |
| WO | WO 2004/011072 A1 | 2/2004 |
| WO | WO 2004/020031 A1 | 3/2004 |
| WO | WO 2005/011785 A1 | 2/2005 |
| WO | WO 2005/021076 A2 | 3/2005 |
| WO | WO 2005/050523 A2 | 6/2005 |
| WO | WO 2007/051230 A1 | 5/2007 |
| WO | WO 2008/055308 A1 | 5/2008 |
| WO | WO 2008/058328 A1 | 5/2008 |
| WO | WO 2008/060295 A2 | 5/2008 |
| WO | WO 2008/076230 A2 | 6/2008 |
| WO | WO 2009/002004 A1 | 12/2008 |
| WO | WO 2009/022004 A2 | 2/2009 |
| WO | WO 2009/146484 A1 | 12/2009 |
| WO | WO 2010/031126 A1 | 3/2010 |
| WO | WO 2010/031125 A9 | 5/2010 |
| WO | WO 2011/059622 A1 | 5/2011 |
| WO | WO 2011/151739 A1 | 12/2011 |
| WO | WO 2012/065999 A2 | 5/2012 |
| WO | WO 2012/080941 A1 | 6/2012 |
| WO | WO 2012/087644 A2 | 6/2012 |
| WO | WO 2012/100291 A1 | 8/2012 |
| WO | WO 2012/065999 A3 | 10/2012 |
| WO | WO 2012/164407 A1 | 12/2012 |
| WO | WO 2013/026901 A2 | 2/2013 |
| WO | WO 2013/045575 A1 | 4/2013 |
| WO | WO 2013/045586 A1 | 4/2013 |
| WO | WO 2013/049660 A2 | 4/2013 |
| WO | WO 2013/050907 A1 | 4/2013 |
| WO | WO 2013/127474 A1 | 9/2013 |
| WO | WO-2013137753 A1 * | 9/2013 ............. G01F 23/26 |
| WO | WO 2013/147623 A1 | 10/2013 |
| WO | WO 2013/148734 A1 | 10/2013 |
| WO | WO 2013/162386 A1 | 10/2013 |
| WO | WO-2013162386 A1 * | 10/2013 .......... A61M 16/024 |
| WO | WO 2013/170290 A1 | 11/2013 |
| WO | WO 2014/055407 A1 | 4/2014 |
| WO | WO 2014/077706 A1 | 5/2014 |
| WO | WO 2014/142677 A1 | 9/2014 |
| WO | WO 2014/205513 A1 | 12/2014 |
| WO | WO 2015/038013 A1 | 3/2015 |
| WO | WO 2015/060729 A1 | 4/2015 |
| WO | WO 2015/093989 A1 | 6/2015 |
| WO | WO 2015/160268 A1 | 10/2015 |
| WO | WO 2016/042522 A1 | 3/2016 |
| WO | WO 2016/089224 A1 | 6/2016 |
| WO | WO 2016/139645 A1 | 9/2016 |
| WO | WO 2017/027906 A1 | 2/2017 |
| WO | WO 2017/126980 A2 | 7/2017 |

OTHER PUBLICATIONS

International Search Report and Written Opinion in PCT/NZ2015/050193 dated Mar. 1, 2016 in 12 pages.

* cited by examiner

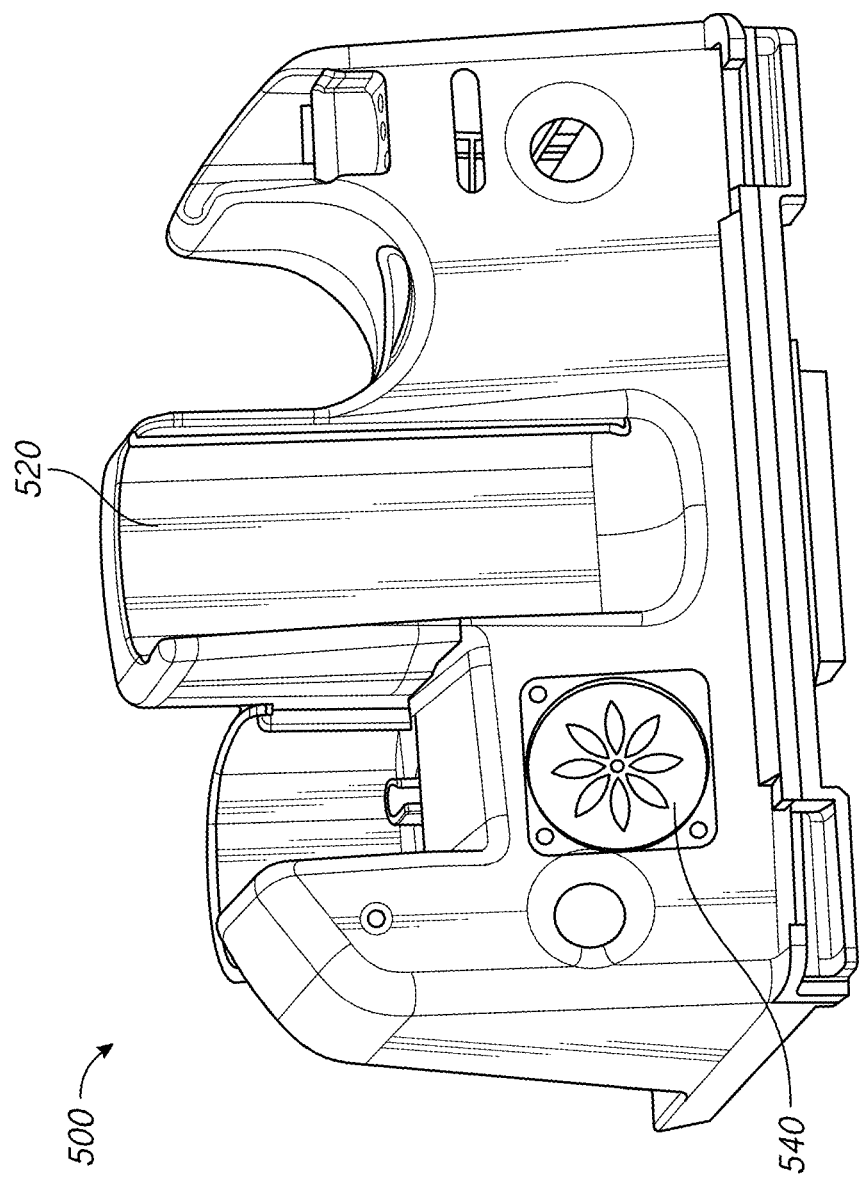

| 1st try (Aluminium impression) (n>3) | Zone 1 | Zone 2 | Zone 3 | Zone 4 |
|---|---|---|---|---|
| P(um) | 150 | 150 | 150 | 150 |
| H(um) | 102 | 115 | 147 | 170 |
| W(um) | 36 | 22 | 9 | 11 |
| R(um) | 25 | 27 | 27 | 27 |
| Φ(deg) | 45 | 45 | 33 | 26 |
| Critical wetting angle $\theta_C$ (deg) | 62 | 64.4 | 66.4 | 66.4 |
| $L_f$@{θ=25°} (mm) | 105 | 118 | 118 | 100 |

Contact angle measurements
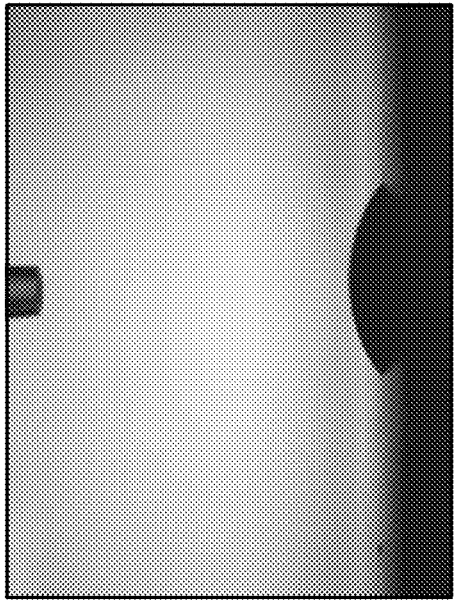
Polycarbonate: θ=68°
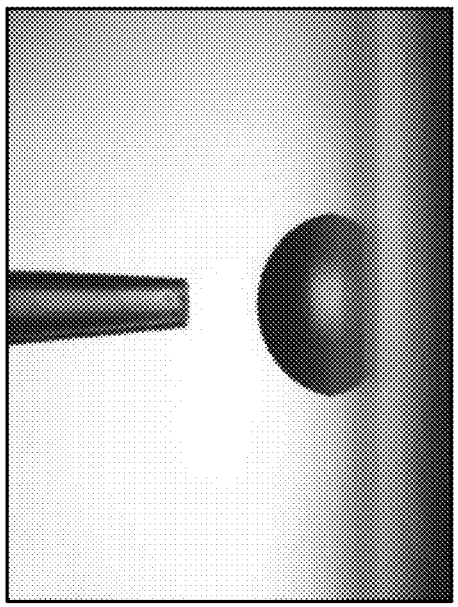
Arnitel VT3108 (@RH=0%): θ=25°
FIG. 13

1602

HUMIDIFICATION OF RESPIRATORY GASES

INCORPORATION BY REFERENCE TO ANY PRIORITY APPLICATIONS

The present application is a national stage application based on International Application No. PCT/NZ2015/050193, filed Nov. 17, 2015, which claims the priority benefit of U.S. Provisional Application No. 62/080,814, filed Nov. 17, 2014, the entirety of which is hereby incorporated by reference herein. Any and all applications for which a foreign or domestic priority claim is identified in the Application Data Sheet as filed with the present application are hereby incorporated by reference under 37 CFR 1.57.

FIELD OF THE DISCLOSURE

The present disclosure generally relates to humidifying respiratory gases. More particularly, the present disclosure relates to a humidification apparatus that promotes heat loss from the humidification chamber.

BACKGROUND

A humidification apparatus is used to provide heated and humidified respiratory gases to a patient via a patient interface. Respiratory gases delivered to a patient at 100% relative humidity and 37° C. mimic the transformation of air that occurs as the respiratory gases pass through the upper airway to the lungs. This may promote efficient gas exchange and ventilation in the lungs, aid defense mechanisms in the airway and increase patient comfort during treatment.

Respiratory gases entering a humidification apparatus are heated and humidified by passing over the surface of the liquid within the humidification chamber. Thus, they are substantially saturated with vapour when they flow out of the humidification chamber through the outlet port. A controller determines the amount of power to supply to the heater so that the respiratory gases comprise a predetermined characteristic such as temperature, humidity or flow at the outlet port. The characteristic can be measured by one or more sensors at the outlet port. Therefore, the humidification apparatus heats and humidifies the respiratory gases so that they are substantially saturated and comprise a predetermined characteristic as they exit the humidification apparatus.

BRIEF SUMMARY

A respiratory assistance system is disclosed that comprises mechanisms to increase heat loss from a humidification chamber to a surrounding ambient environment.

An embodiment discloses a structure that couples to a humidification apparatus and at least partially encloses the humidification chamber. The structure comprises integrated sensors that protrude from the structure and extend at least partially into the humidification chamber. The structure comprises alignment and orientation features to better facilitate coupling with the humidification chamber.

In some embodiments, the structure includes alignment features, such as a shroud and a hood. The shroud facilitates coupling with an inspiratory tube connector. The hood aligns with a corresponding nose of the humidification chamber. The hood further comprises rails that aid in alignment of the humidification chamber. The hood comprises an opening that allows heat loss from the humidification chamber to the surrounding ambient environment. The sensors are positioned both within the shroud, and on a post, which provides a platform to allow sensing within the humidification chamber.

In some embodiments optional to any embodiment disclosed herein, the structure includes an active cooling mechanism that acts to blow air on or around the humidification chamber. An example of an active cooling mechanism is a fan.

The humidification chamber includes apertures that can receive the sensors. In some embodiments optional to any embodiment herein, the humidification chamber includes a passive cooling mechanism. The passive cooling mechanism is in the form of a heat sink, for example, fins. The fins protrude from the humidification chamber and extend in an upward direction. The fins encourage additional heat loss from the humidification chamber.

In some embodiments optional to any embodiment disclosed herein, the humidification chamber includes a wall that bulges outwardly from between the base and an upper surface of the humidification chamber. This increases the surface area of the liquid within the humidification chamber, which increases the amount of humidity that is transferred to the respiratory gases. In some embodiments optional to any embodiment disclosed herein, a humidification chamber may be used that includes altered geometries such that the surface area of the liquid is optimised.

In some embodiments optional to any embodiment disclosed herein, regions of the humidification chamber include a thermally conductive material. This facilitates heat loss from the humidification chamber without altering the overall geometry or size of the humidification chamber.

BRIEF DESCRIPTION OF THE DRAWINGS

These and other features, aspects, and advantages of the present disclosure will be described with respect to the following figures, which are intended to illustrate and not to limit the disclosed embodiments.

FIG. 6 is a perspective view of a structure according an embodiment of the present disclosure.

FIG. 13 shows contact angle measurements for two different materials that can be used to make the cooling structures.

DETAILED DESCRIPTION

Figure 1:
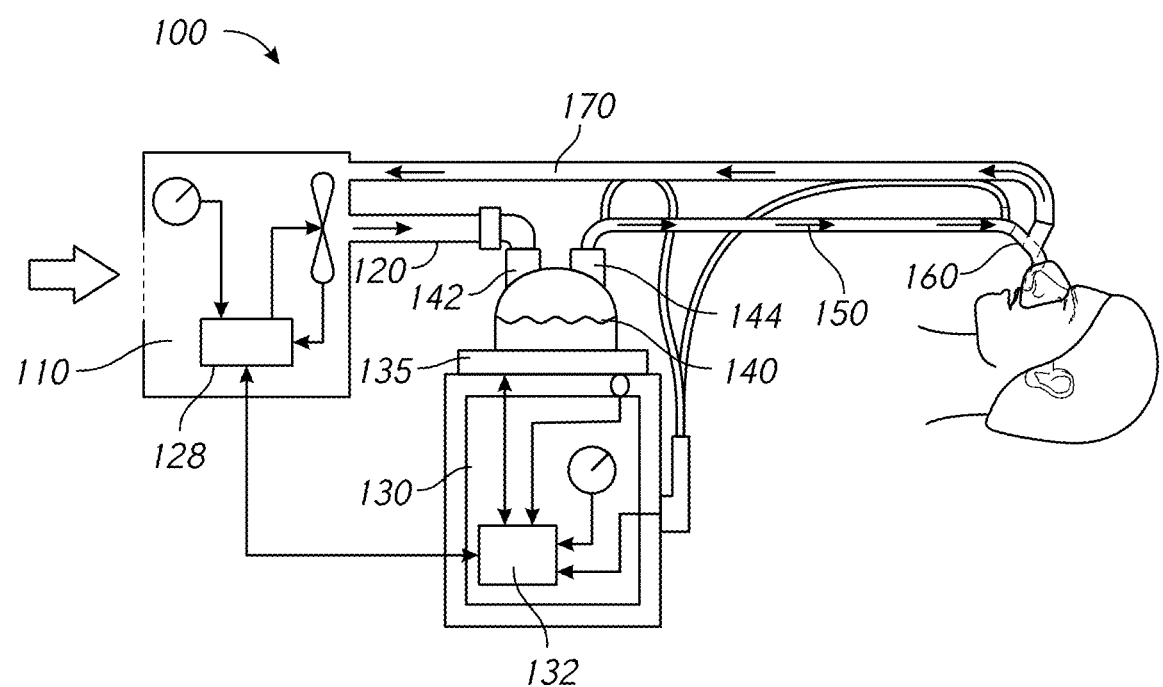
FIG. 1 is a schematic of a respiratory assistance system

FIG. 1 discloses a respiratory assistance system 100 that includes a gases source 110. The gases source 110 utilises a gases supply tube 120 to supply respiratory gases to a humidification apparatus 130. In some embodiments, the gases source 110 and the humidification apparatus 130 are within the same housing. In some embodiments, the gases source 110 and the humidification apparatus 130 are in different housings. The humidification apparatus 130 includes a base unit 135 and a humidification chamber 140. The humidification chamber 140 can be mounted on the base unit 135. The humidification chamber 140 can hold a volume of liquid, for example, water. The humidification chamber 140 further includes an inlet port 142 and an outlet port 144. Respiratory gases are humidified as they pass through the humidification chamber 140 via the outlet port 144 and into an inspiratory tube 150 where they are transported to a patient interface 160. In some embodiments, an expiratory tube 170 transports exhaled gases away from a patient.

Respiratory gases entering the humidification chamber 140 are heated and humidified by passing over the surface of the liquid. Thus, they are substantially saturated with vapour when they exit the humidification chamber 140 through the outlet port 144. The base unit 135 includes a heater plate 240. A controller 132 of the humidification apparatus 130 determines the amount of power to supply to the heater plate 240 to heat the humidification chamber 140 when the humidification chamber 140 is mounted on the base unit 135 so that the respiratory gases include a predetermined characteristic at the outlet port 144 as measured by a sensor (not shown in FIG. 1) at or near the outlet port 144. Therefore, the humidification apparatus 130 acts to heat and humidify the respiratory gases so that they are substantially saturated and include a predetermined characteristic. In some embodiments, a controller 128 of the gases source 110 may communicate with the controller 132 as part of the operations of the controller 132 herein described. In some embodiments, the controller 128 may execute part or all of the operations of the controller 132 herein described.

In some embodiments, the predetermined characteristic is a gases temperature. In some embodiments, the predetermined characteristic may be a relative humidity, an absolute humidity, or a flow rate of gases. The temperature of the respiratory gases at the inlet port 142 is typically less than a temperature of the respiratory gases at the outlet port 144. Thus, a temperature differential exists between the inlet port 142 and the outlet port 144. This, in effect, is a temperature differential that exists between the incoming gases and the outgoing gases, respectively. The controller 132 determines how much power to supply to the heater plate 240 to bring the temperature of the respiratory gases to a value similar to the predetermined temperature at the outlet port 144. As the heater plate 240 heats the respiratory gases to the predetermined temperature, the respiratory gases can be humidified during the process of heating.

In some cases, the temperature of the respiratory gases at or near the outlet port 144 may already be at or close to the predetermined temperature. This may be due to a high ambient temperature, gases supplied from the gases source 110 to the humidification apparatus 130 at a higher temperature, heating effects from within the humidification apparatus 130, or heating effects from within the gases source 110. As a result, the controller 132 determines that less heating is necessary to heat the respiratory gases to the predetermined temperature and supplies less power to the heater plate 240. Thus, although the respiratory gases leaving the humidification chamber 140 are substantially similar to the predetermined temperature, less humidity is added to the respiratory gases.

The humidification apparatus 130 includes mechanisms to facilitate heat loss from the humidification chamber 140 to allow a greater temperature differential between the inlet port 142 and the outlet port 144. A greater temperature differential causes more power to be supplied to the heater plate 240 to heat the respiratory gases. This allows more humidity to be added to the respiratory gases. In some embodiments, a structure 220 includes mechanisms to promote heat loss. In some embodiments, the humidification chamber 140 includes mechanisms to improve heat loss. The mechanism may correspond to a shape, design, or an insert.

Figure 2:
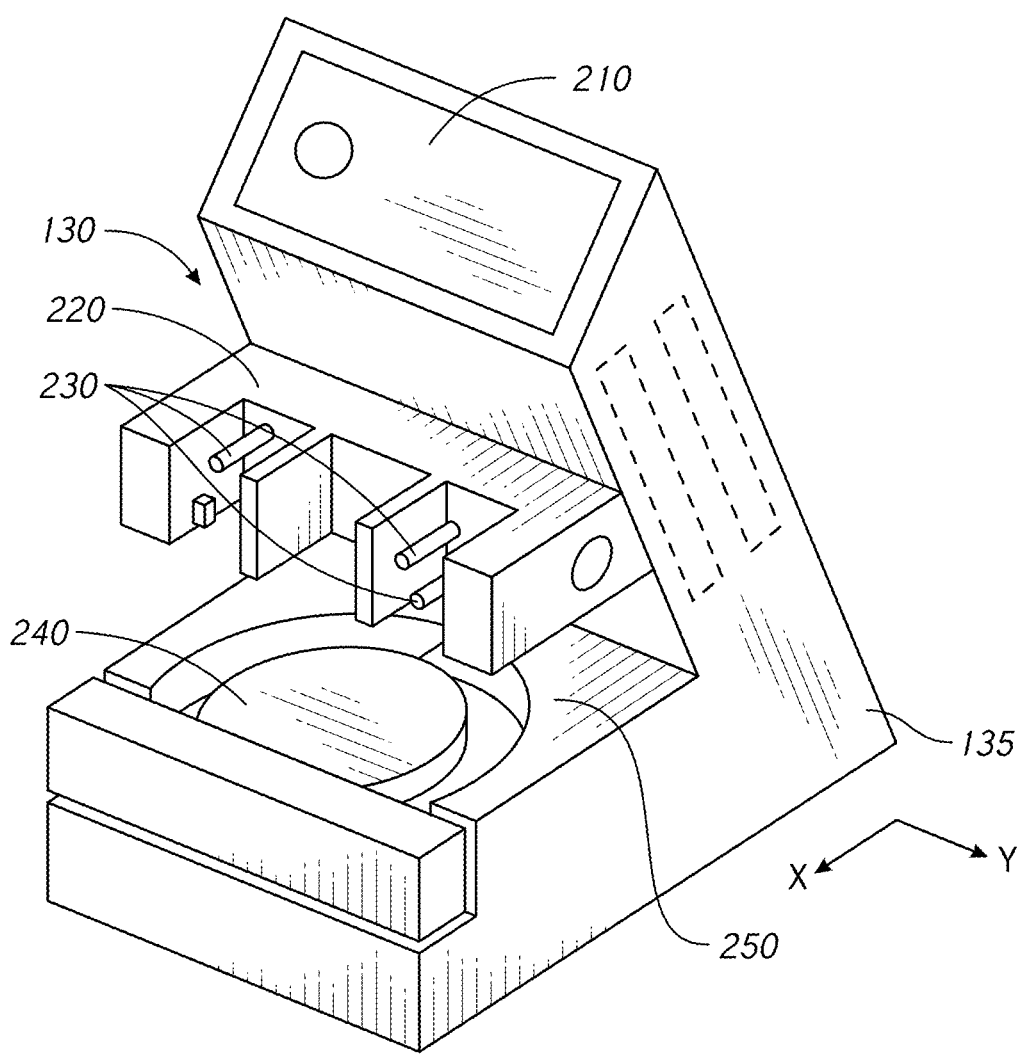
FIGS. 2-3 are perspective views of a humidification apparatus according to an embodiment of the present disclosure.
Figure 3:
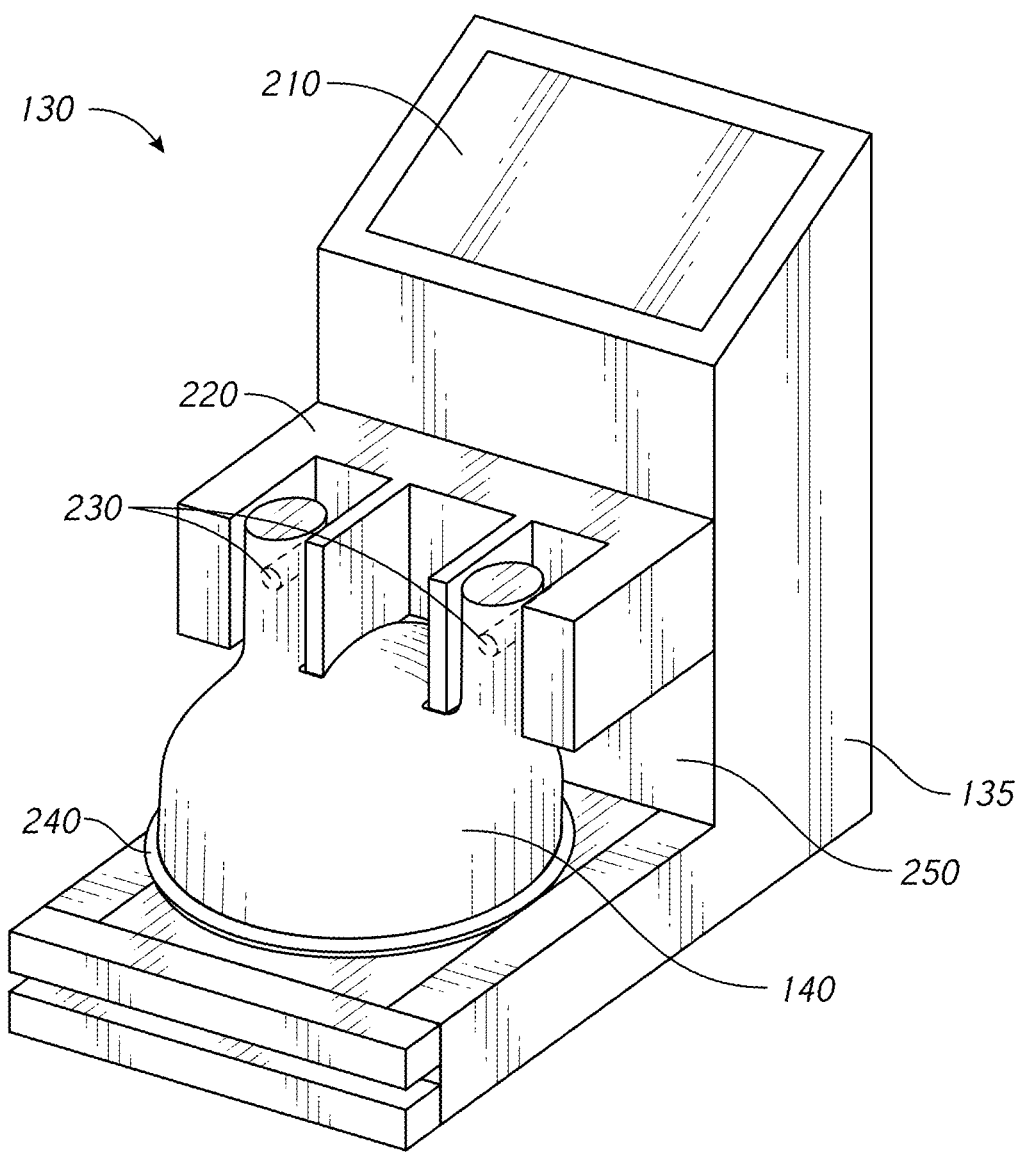

FIGS. 2-3 illustrate an embodiment of the humidification apparatus 130 that includes the base unit 135, a display 210, the structure 220, the humidification chamber 140, and the heater plate 240. The structure 220 includes sensors 230. In some embodiments, the sensors 230 are permanently mounted onto the structure 220. In some embodiments, the sensors 230 may be removably coupled to the structure 220. The sensors 230 may be positioned to protrude into the inlet port 142 and/or the outlet port 144 when the humidification chamber 140 is mounted on the base unit 135. In the illustrated embodiment, two of the sensors 230 are positioned to measure at least one characteristic of the gases flow at the inlet port 142, and one of the sensors 230 is positioned to measure at least one characteristic of the gases flow at the outlet port 144. In some embodiments, one of the sensors 230 is positioned to measure at least one characteristic of the gases flow at the inlet port 142, and two of the sensors 230 are positioned to measure at least one characteristic of the gases flow at the outlet port 144, when the humidification chamber 140 is mounted on the base unit 135. In some embodiments, two of the sensors 230 are positioned to measure at least one characteristic of the gases flow at the inlet port 142, while one sensor is positioned at the outlet port 144. The sensors 230 can also be arranged in other configurations with different combinations at the inlet port 142 and the outlet port 144. The structure 220 can also include more than 3 sensors or less than 3 sensors.

In some embodiments, the sensors 230 are mounted in planes parallel or substantially parallel with respect to each other. Further, the sensors 230 can be oriented in the same direction with respect to each other. In the illustrated embodiment in FIG. 2, the sensors 230 are situated parallel to the x-y plane and extend along the x-axis. In some embodiments, the placement of the sensors 230 advantageously enables for the humidification chamber 240 to slide into the humidification apparatus 130 with respect to the structure 220 (as shown in FIG. 3). Moreover, as seen in FIG. 2, the sensors 230 are all placed perpendicular to a vertical plane. Two of the sensors 230 are positioned in a different but substantially parallel horizontal planes. Accordingly, one of these sensors may measure characteristic of a gas at a different point in time as the gas flows through the humidification chamber 140 because of the difference in location. That is, a first sensor is positioned such that the gas passes over it shortly before the gas passes over the second sensor. In some embodiments, two of the sensors 230 may be mounted in the same horizontal plane or substantially the same horizontal plane so that the sensors 230 can measure characteristic of the gas flow at the same time. In some embodiments, if the sensors are measuring different characteristics, it may be advantageous to have them measure the characteristics at the same point in time of gas flow for the purposes of comparison.

Further, FIG. 3 illustrates the humidification chamber 140 attached to the base 135. As seen from the figure, some of the portions of the humidification chamber 140 are occluded or covered by the base 135, particular the top portions of the humidification chamber 140. The covered portions may act as an insulator for the humidification chamber 140 and trap heat inside the humidification chamber 140. Accordingly, in some embodiments, it may be advantageous to have more surface area of the humidification chamber 140 exposed to the air to avoid the insulation effect. In an embodiment, the base 135 as illustrated herein is designed to increase exposure of the surface area of the humidification chamber 140 to external environment. For example, in the embodiments illustrated, about 45% to about 50% of the chamber is exposed as viewed from the top. In some embodiments, about 40% to about 45% of the chamber is exposed as viewed from the top. The base 135 and the humidification chamber 140 can also be designed to expose more than 50%, such as 60% or 70% of the chamber. In some embodiments, the percentage can be calculated by measuring the entire surface area of the humidification chamber 140 and dividing the exposed surface area by the entire surface area.

In some embodiments, the sensors 230 each may measure one of temperature, flow rate, or humidity. In some embodiments, the sensors 230 may measure a combination of any one of temperature, flow rate, and humidity. In some embodiments, two of the sensors 230 may be used in combination to derive a characteristic of the gases flow; for example, two of the sensors 230 may be positioned to measure gases temperature at the inlet port 142, and the controller 132 may use the two measurements to derive a flow rate of the gases. In some embodiments, one of the sensors 230 may be positioned downstream of the humidification apparatus 130, for example, near the patient interface 160. In some embodiments, one of the sensors 230 may be positioned at the heater plate 240.

Heating of the heater plate 240 is controlled by the controller 132. The controller 132 determines the amount of power required to provide sufficient heat to the liquid within the humidification chamber 140. The surface of the heater plate 240 is in contact with a thermally conductive surface of the humidification chamber 140. This provides a thermally conductive pathway to enable the transfer of heat from the heater plate 240 to the liquid within the humidification chamber 140.

In some embodiments, the structure 220 is removably coupled to the base unit 135. In some embodiments, the structure 220 may be permanently coupled to the base unit 135. In some embodiments, the structure 220 may be integrally formed with the base unit 135. The structure 220 can form a support structure for the sensors 230. The structure 220 includes features that aid with alignment and orientation of the humidification chamber 140 relative to the base unit 135 and/or the sensors 230, which will be discussed in further detail below, and as described in the embodiments disclosed in U.S. Provisional Patent Application No. 62/059,339 and International Application No. PCT/NZ2014/000201, the contents of which are hereby incorporated by reference in their entirety.

The structure 220 is coupled to or integral with a portion of the base unit 135 that is positioned above the heater plate 240. This positions electronic components within the base unit 135 and electronic components within the structure 220 above likely leak points of the humidification chamber 140 when the humidification chamber 140 is mounted on the base unit 135 in contact with the heater plate 240. The display 210 is positioned on an upper surface of the base unit 135 above the structure 220. This increases visibility of the display 210 in use. As a result, the humidification chamber 140 is mounted within a recess 250 formed by the base unit 135. The structure 220 at least partially encloses the humidification chamber 140 within the recess 250. This enables the sensors 230 to protrude into the inlet port 142 and/or the outlet port 144 of the humidification chamber 140 to determine a characteristic of the gases flow. As discussed above, the orientation and placement of the sensors 230 can enable the humidification chamber 140 to be mounted within the recess 250.

Figure 4:
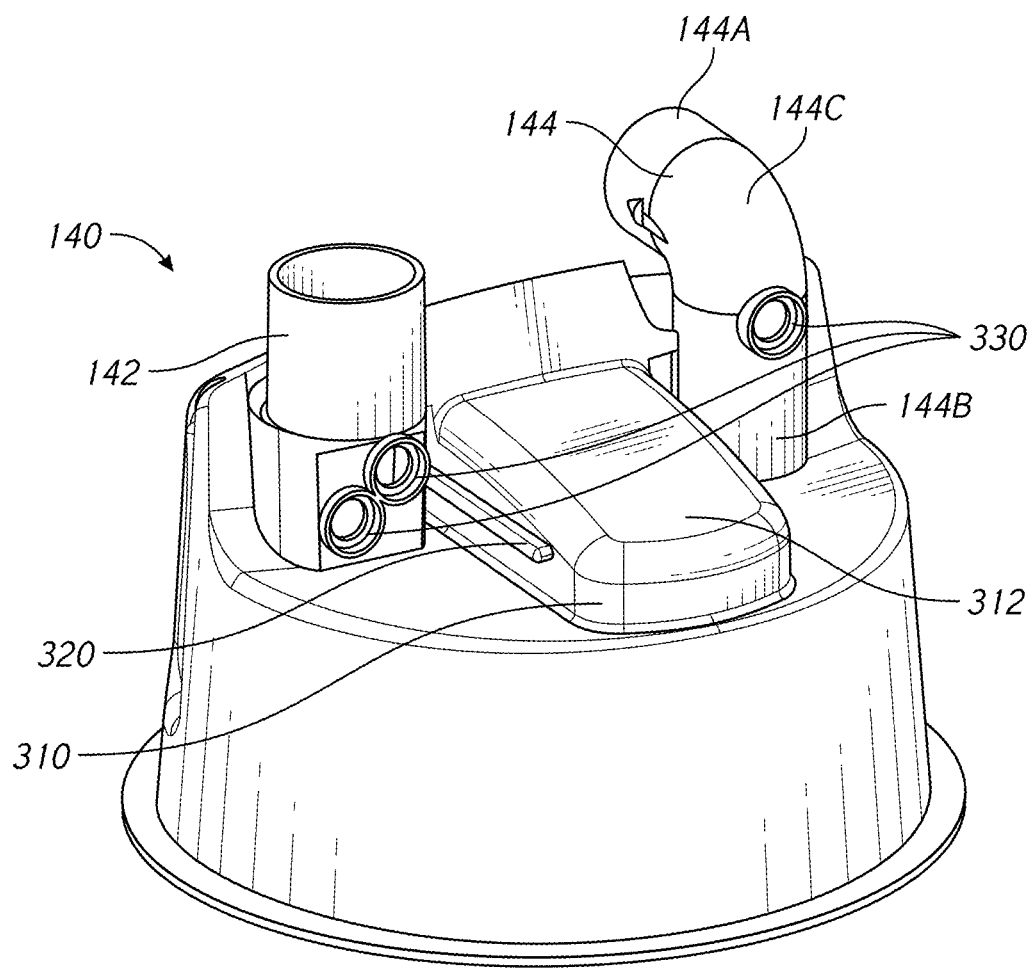
FIG. 4 is a perspective view of a humidification chamber according to an embodiment of the present disclosure.
Figure 5A:
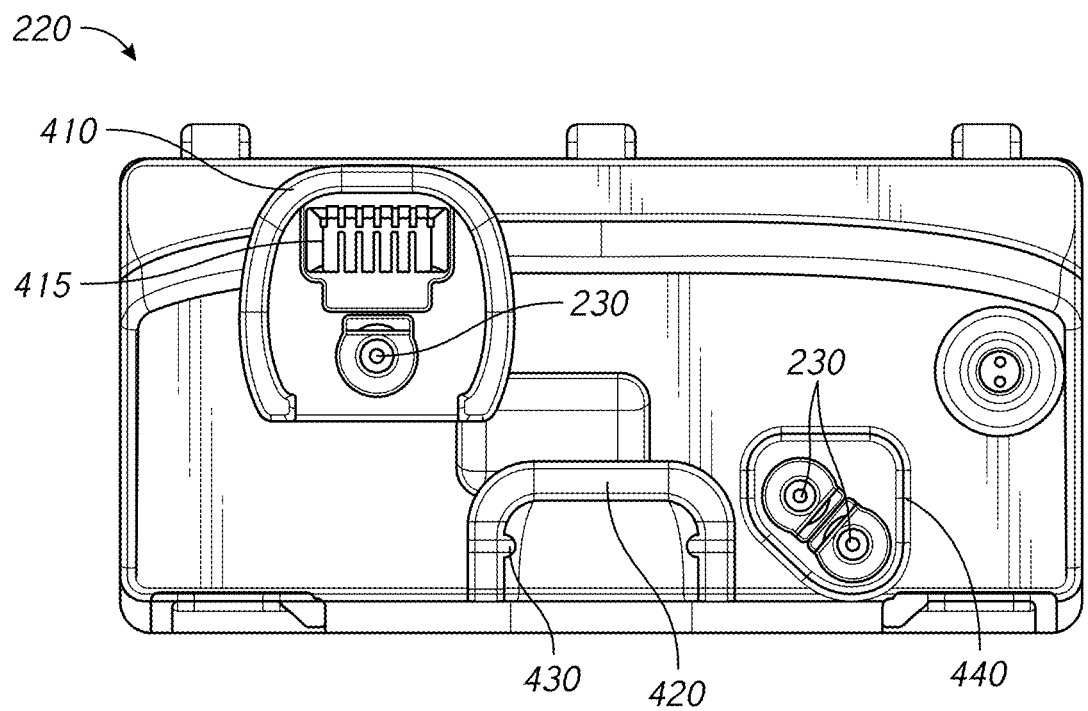
FIG. 5A is a front perspective view of a structure according to an embodiment of the present disclosure.
Figure 5B:
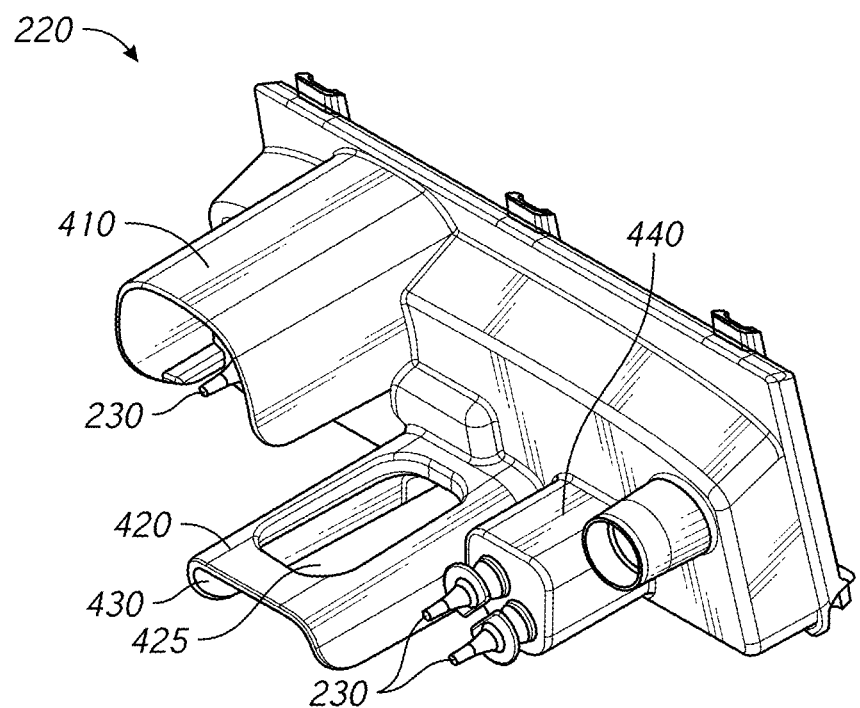
FIG. 5B is an isometric view of a structure according to the embodiment of FIG. 5A.

FIG. 4 illustrates the humidification chamber 140 in more detail. The humidification chamber 140 includes a nose 310 and apertures 330. The nose 310 mates with a corresponding hood 420 (as shown in FIGS. 5A-5B). The nose 310 aids alignment between the humidification chamber 140 and the structure 220. In some embodiments, the nose 310 includes rails 320, which mate with corresponding grooves 430 in the structure 220 (as shown in FIGS. 5A-5B). The rails 320 also aid alignment between the humidification chamber 140 and the structure 220. In some embodiments, the nose 310 does not include the rails 320 and the structure 220 does not include the grooves 430. In some embodiments, the tongue 312 of the nose 310 is tapered. The tapered tongue 312 can advantageously prevent the humidification chamber 140 from rocking with respect to the hood 420. Rocking may result in disconnection of sensors 230.

The apertures 330 can receive the sensors 230 that are positioned on the structure 220 (refer to FIGS. 5A-5B). Thus, when the humidification chamber 140 is mounted on the base unit 135, the sensors 230 protrude into the apertures 330 of the humidification chamber 140. The sensors 230 measure a characteristic of the gases flow in the humidification chamber 140 through the apertures 330. The apertures 330 are positioned at or near the inlet port 142 and/or outlet port 144 of the humidification chamber 140. In some embodiments, the apertures 330 each further include a seal or barrier (not shown) to maintain a sealed pathway for the gases flow. The seal can be an o-ring. In some embodiments, the apertures 330 can include a grommet or an elastic glove that can protect the sensors 230 as they are inserted into the apertures 330.

In the illustrated embodiment, two of the apertures 330 are positioned near the inlet port 142 and one of the apertures 330 is positioned near the outlet port 144. In some embodiments, one of the apertures 330 is positioned near the inlet port 142 and two of the apertures 330 are positioned near the outlet port 144. In some embodiments, variations or different combinations of the apertures 330 may be positioned at or near each port. For example, multiple of the apertures 330 may be positioned at both the inlet port 142 and the outlet port 144.

As discussed above, In some embodiments, the sensors 230 are oriented in the same direction and positioned in same or parallel planes. Accordingly, the apertures 330 may also be positioned on the humidification chamber 140 such that they align with their respective sensors 230. In some embodiments, the apertures 330 face the same or substantially the same direction as illustrated in FIG. 4. Thus, as the humidification chamber 140 is slid horizontally into the base 135, the sensors 230 align with the apertures 330 and positioned to measure the characteristics of gas flow at particular locations near the inlet port 142 and the outlet port 144. As a result, the sensors are all positioned within the chamber in a single connection step by a user such that the user does not need to separately position the sensors in the chamber as is required by prior art devices.

In some embodiments, the outlet port 144 (FIG. 4) includes a vertical portion 144b and a horizontal portion 144a connected by a curved portion 144c. While the illustrated embodiment shows an L-shape or a right angle, the angle between horizontal portion 144a and the vertical portion 144b can be greater than 90 degrees. Higher angles may make the transition from the vertical portion 144b to the horizontal portion 144a smoother and as a result may decrease turbulence in the air moving from the vertical portion 144b to the horizontal portion 144a. In some embodiments, the horizontal portion 144a may advantageously enable a user to connect a conduit with the humidification chamber 140 either before the humidification chamber 140 is attached to the base 135 or after the attachment with the base 135. In some embodiments, the inlet port 142 can also include a vertical portion, a horizontal portion, and a curved portion as discussed above with respect to the outlet port.

FIGS. 5A-5B illustrate different views of an embodiment of the structure 220. The structure 220 includes a shroud 410, the hood 420, the sensors 230, and a post 440. The shroud 410 can receive a connector, for example, a connector configured to connect the inspiratory tube 150 to the humidification apparatus 130. In some embodiments, the connector is configured to form an electrical connection between the inspiratory tube 150 and the humidification apparatus 130. In some embodiments, the connector is configured to form an electrical connection with the structure 220, and the structure 220 is configured to form an electrical connection with the base unit 135. As a result, the structure 220 includes electrical contacts 415 within the shroud 410, as shown in more detail in FIG. 5A. The shroud 410 helps to align the connector of the inspiratory tube 150 with the structure 220. The shroud 410 facilitates pneumatic coupling between the inspiratory tube 150 and the outlet port 144 of the humidification chamber 140. In the illustrated embodiment, the structure 220 includes one of the sensors 230 within the shroud 410. Thus, as connection is made between the structure 220, the connector of the inspiratory tube 150, and the outlet port 144 of the humidification chamber 140, the one of the sensors 230 within the shroud 410 protrudes into the outlet port 144 and an electrical connection is formed between the inspiratory tube 150 and the humidification apparatus 130. In some embodiments, the shroud 410 protects the electrical contacts 415 from spills or other environmental conditions.

With continued reference to FIGS. 5A-5B, the hood 420 can accommodate the nose 310 of the humidification chamber 140. In some embodiments, the hood 420 includes grooves 430 to mate with the optional rails 320 that protrude from the nose 310 of the humidification chamber 140. The hood 420 can include an optional opening 425. The opening 425 allows heat energy from the humidification chamber 140 to dissipate to the surrounding ambient environment. Thus, the opening 425 reduces the mechanical contact between the humidification chamber 140 and the structure 220. This improves cooling of the humidification chamber 140 as it is further isolated from the structure 220.

In the illustrated embodiment, the post 440 includes two of the sensors 230. Thus, the post 440 provides a platform that facilitates coupling of the two of the sensors 230 with two of the apertures 330 that are associated with the inlet port 142 of the humidification chamber 140. The post 440 enables the two of the sensors 230 to protrude into the two of the apertures 330 of the inlet port 142. This enables the two of the sensors 230 to more accurately determine a characteristic of the gases flow.

In some embodiments, the controller 132 adjusts the power supplied to the heater plate 240 for adding energy into the respiratory assistance system 100. The added energy from the heater plate 240 can evaporate liquid in the humidification chamber 140. The evaporated liquid can add humidity to the respiratory gases. In some embodiments, the controller 132 can continue to supply power to the heater plate 240 until a characteristic of the respiratory gases at the outlet port 144 reaches a predetermined output condition, or a set point. The characteristic of the respiratory gases at the outlet port 144 can be measured by the sensors 230 (discussed above) at the outlet port 144. In some embodiments, the characteristic of the respiratory gases can be measured at other locations in the respiratory assistance system 100. For example, the characteristic of the respiratory gases can be measured at the patient interface 160. In some embodiments, characteristics of respiratory gases can include humidity, temperature, and flow rate.

In some embodiments, the respiratory assistance system 100 does not include a humidity sensor to directly measure humidity conditions of the respiratory gases. In such an embodiment, the controller 132 can control the heater plate 240 to deliver a target humidity condition using temperature and/or flow rate measurements provided by the sensors 230 to estimate humidity conditions of the respiratory gases delivered by the humidification apparatus 130 and to use such estimated humidity conditions to control the heater plate 240 to generate humidity. Some conditions of the gases supplied to the humidification apparatus 130 by the gases source 110 may compromise the ability of the humidification apparatus 130 to add sufficient humidity.

In some embodiments, the controller 132 relying on estimated humidity conditions based on temperature measurements to control the heater plate 240 may result in compromised humidity generation. For example, when the gases source 110 is drawing in ambient gases to supply to the humidification apparatus 130, the characteristics of the gases drawn in by the gases source 110 can fluctuate depending on ambient conditions. In a desert environment, the ambient air may have high temperature and low humidity. When respiratory gases enter the humidification chamber 140, the controller 132 may initially provide power to the heater plate 240 to add heat to the liquid in the humidification chamber 140 to evaporate liquid and add humidity to the gases; however, when the incoming gases are already at a high temperature, the controller 132 may stop providing power to the heater plate 240 before sufficient humidity or vapor has been added to the respiratory gases. Consider an instance where the temperature of the ambient gases drawn in by the gases source 110 is 34 degrees Celsius and the set point temperature of the gases at the outlet port 144 is 37 degrees Celsius. The controller 132 may provide power to the heater plate 240 until the respiratory gases reaches 37 degrees at the outlet port 144. However, since the ambient gases temperature is already close to the set point temperature, the heater plate 240 may not need to add much heat for the respiratory gases to reach the set point temperature. The amount of heat needed may not be enough. In particular, if the incoming ambient gas is dry, the gases delivered at the patient interface 160 may not have sufficient humidity for patient comfort.

Moreover, humidity addition may further be compromised because of the flow rate of the gases and the design constraints of the respiratory assistance system 100. In some embodiments, a high flow therapy may be required. Accordingly, there may be even less time to add humidity to the gases because of the higher flow. Furthermore, there may be competing constraints of reducing the size of the humidification chamber 140 and the available surface area of the liquid interacting with the volume of respiratory gases in the humidification chamber 140. Accordingly, in some embodiments, it may be advantageous to decrease the temperature of the respiratory gases. Further, in some embodiments, it may be advantageous to increase the surface area of liquid interacting with the volume of the respiratory gases flowing through the humidification chamber 140. The humidification chamber 140 can be modified as described below to improve heat transfer and/or increase surface area between the liquid and the flowing respiratory gases.

The structure 220 at least partially encloses the humidification chamber 140 when it is mounted on the base unit 135. As discussed, features on the structure 220 facilitate coupling of the humidification chamber 140 with the sensors 230 to provide more accurate determinations of characteristics of the gases flow. The features on the structure 220 also aid with alignment and orientation of the humidification chamber 140 with respect to the base unit 135 or the sensors 230. The humidification chamber 140 being partially enclosed facilitates greater heat loss between the humidification chamber 140 and the surrounding ambient environment.

FIG. 6 illustrates an embodiment wherein a structure 500 includes an active cooling mechanism 540 to facilitate heat loss from the humidification apparatus 130 to the surrounding ambient environment. The active cooling mechanism 540 moves air onto and around the humidification chamber 140. This encourages heat loss from the humidification chamber 140 to the surrounding ambient environment. In some embodiments, the active cooling mechanism 540 includes a fan. In some embodiments, the active cooling mechanism 540 may include a blower. In some embodiments, the structure 500 includes an air inlet to allow the active cooling mechanism 540 to draw air into the structure 500 from the surrounding ambient environment. In some embodiments, the structure 500 includes an air outlet to allow the active cooling mechanism 540 to expel air from the structure 500 out to the surrounding ambient environment. The active cooling mechanism 540 may aid heat loss in the structure 500.

In the illustrated embodiment, the structure 500 including the active cooling mechanism 540 provides an increased enclosure effect on the humidification chamber 140 relative to the structure 220 illustrated in FIGS. 5A-5B. For example, a hood 520 does not include an opening such as the opening 425 of the hood 420 to encourage further heat loss. In another example, the body of the structure 500 extends such that it interacts more fully with the humidification chamber 140. In some embodiments, the active cooling mechanism 540 may be combined with the structure 220 in FIGS. 5A-5B to further enhance heat loss. In some embodiments, the structure 220 or the structure 500 may include a thermally insulating material to slow the spread of heat therein.

In some embodiments, the thermally insulating material may be combined with the active cooling mechanism 540.

Figure 7:
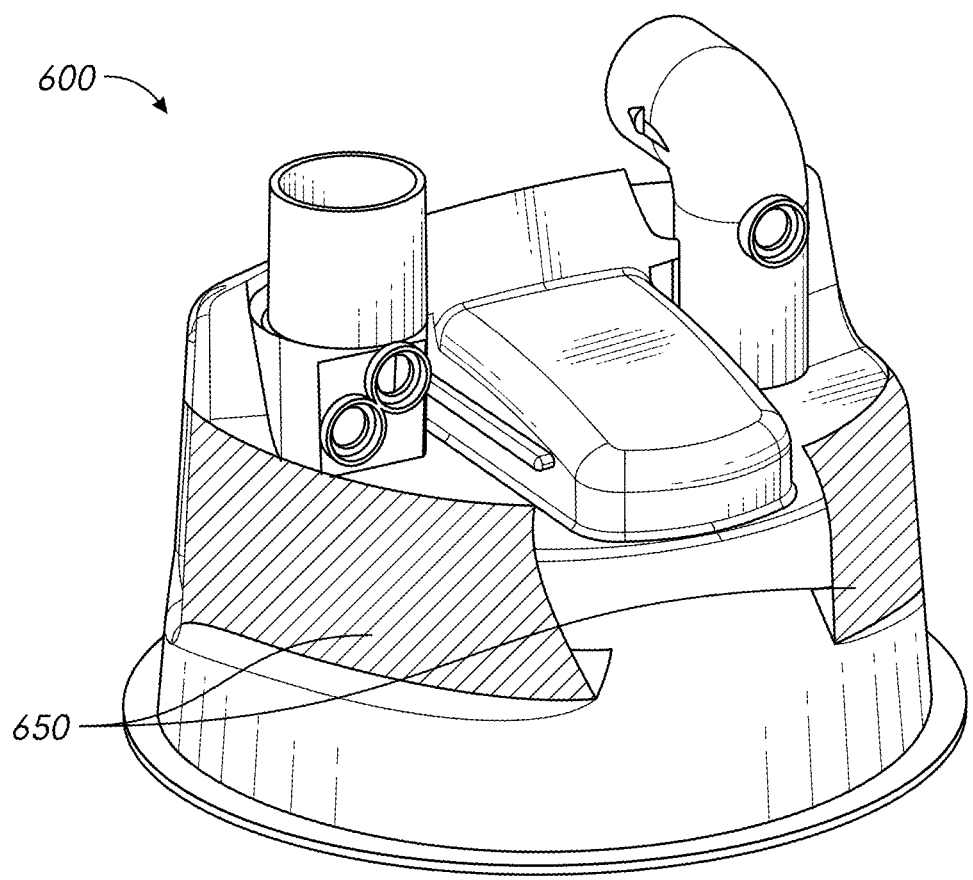
FIGS. 7-9 are perspective views of different embodiments of a humidification chamber.

FIG. 7 is an example of a humidification chamber 600 including a passive cooling mechanism 650. The passive cooling mechanism 650 may be any mechanism that passively encourages heat transfer to occur between the humidification chamber 600 and the surrounding ambient environment, for example, a heat sink including fins or pins. The passive cooling mechanism 650 acts to increase the surface area of the humidification chamber 600 that can be utilised for heat loss.

In some embodiments, the passive cooling mechanism 650 may be permanently coupled to the humidification chamber 600. Permanent coupling of the passive cooling mechanism 650 could be using a snap-fit mechanism, clipping, adhesives or welding mechanisms. In some embodiments, the passive cooling mechanism 650 may be an integral part of the humidification chamber 600. In some embodiments, the passive cooling mechanism 650 may be removably coupled to the humidification chamber 600. Removable coupling of the passive cooling mechanism 650 allows the humidification chamber 600 to couple with different structures, for example, the structure 220 or the structure 500.

In the illustrated embodiment, the passive cooling mechanism 650 includes a fin. In some embodiments, the passive cooling mechanism 650 may include multiple fins. The fin 650 protrudes from the humidification chamber 600 such that the alignment and orientation features of the humidification chamber 600 are still able to facilitate coupling between the humidification chamber 600 and the structure 220.

The fin 650 may comprise the same material as the humidification chamber 600. In some embodiments, the fin 650 may include a more thermally conductive material to further promote heat loss from the humidification chamber 600. The geometry of the fin 650 may depend on the geometry of the structure 220 to which the humidification chamber 600 is to be coupled. For example, In some embodiments, the fin 650 may extend substantially vertically towards the ports of the humidification chamber 600. In some embodiments, the fin 650 may extend substantially horizontally from the humidification chamber 600. A combination of the above geometries may also be used.

Figure 8:
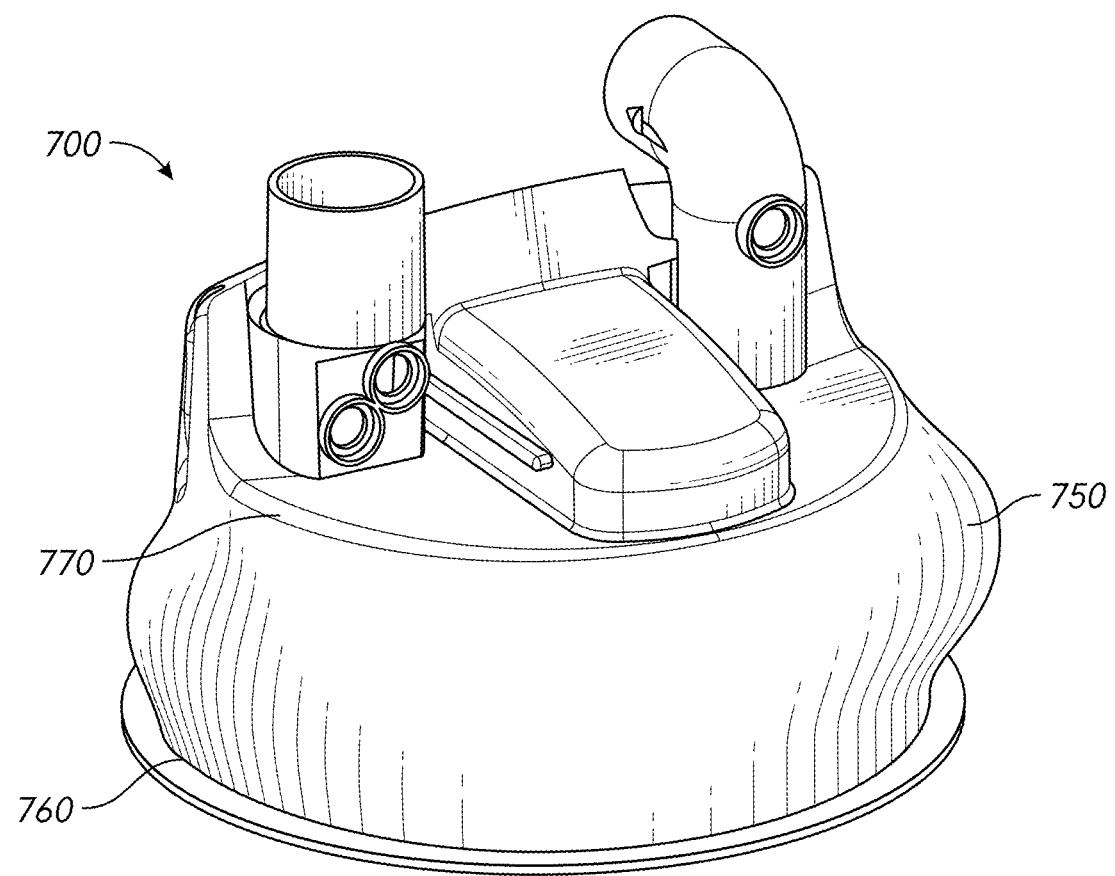

FIG. 8 illustrates an embodiment that includes a wall 750 of a humidification chamber 700 that has been enlarged. The wall 750 includes at least a portion that bulges out between a base 760 and an upper surface 770 of the humidification chamber 700. This increases the surface area of the humidification chamber 700, without substantially increasing its footprint. Thus, a greater amount of humidity is transferred to the respiratory gases. The humidification chamber 700 is mountable on the base unit 135 with minimal or no changes required to the base unit 135. In some embodiments, the humidification chamber 700 may include different geometries that increase the surface area. Increasing the surface area increases the area of contact between the liquid and the respiratory gases, which promotes more efficient humidification of respiratory gases. For example, the size of the humidification chamber 700 may be increased, or the shape of the humidification chamber 700 may be optimised to produce an optimal surface area between the liquid and the respiratory gases. In another example, the interior of the wall 750 may include microstructures as disclosed in International Application No. PCT/NZ2013/000113, the contents of which are hereby incorporated by reference in their entirety.

Figure 9:
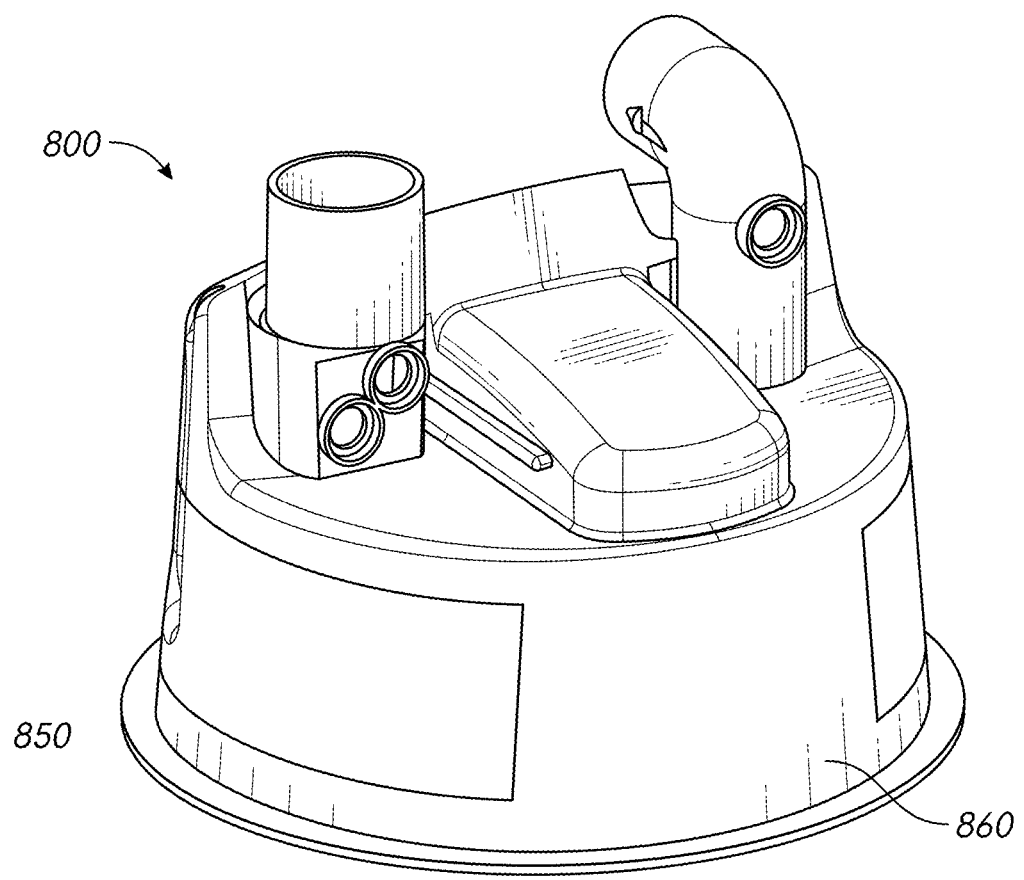

FIG. 9 illustrates an embodiment wherein a humidification chamber 800 includes regions 850 that facilitate improved heat loss. The regions 850 include a material that has a higher thermal conductivity than the material of the humidification chamber 800. In the illustrated embodiment, two regions 850 are utilised. In some embodiments, a single region 850 or multiple regions 850 can be used to encourage heat loss from the humidification chamber 800 to the surrounding ambient environment. In some embodiments, the material may be metal, for example, copper. The regions 850 facilitate greater heat loss through a wall 860 of the humidification chamber 800. This enables heat loss to occur without altering the geometry of the humidification chamber 800. In the illustrated embodiment, the regions 850 are permanently coupled to the humidification chamber 800. In some embodiments, the regions 850 may be integral to the humidification chamber 800. In some embodiments, the entirety of the humidification chamber 800 or the wall 860 of the humidification chamber 800 may be made from thermally conductive material.

Figure 10:
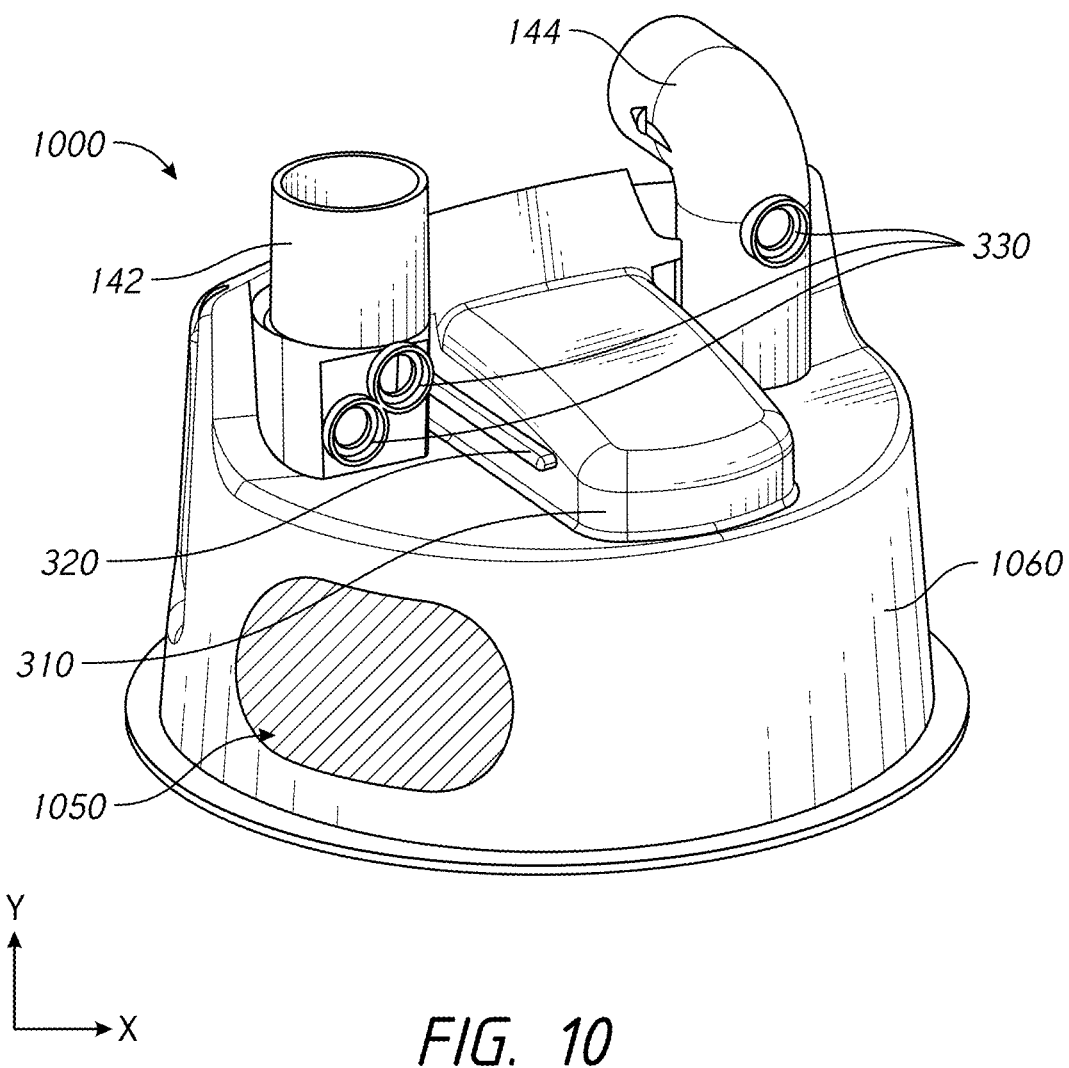
FIG. 10 illustrates an embodiment of a humidification chamber with a cooling structure.

In some embodiments, the humidification chamber 140 may include a cooling structure 1050 as shown in FIG. 10. The cooling structure 1050 can be located inside the humidification chamber 140. In some embodiments, the cooling structure 1050 may be a separate component that can be removably inserted in the humidification chamber 140. The cooling structure 1050 may be secured using a fastener or designed to fit around the shape of the humidification chamber 140. In some embodiments, the cooling structure 1050 is secured against the side walls 1060 of the humidification chamber 1000. The cooling structure 1050 may completely or partially cover the sidewalls 1060. In some embodiments, the cooling structure 1050 is placed near the inlet port 142. In some embodiments, placing the cooling structure 1050 near the inlet port 142 may result in increased humidity generation because of a higher temperature gradient.

Figure 11:
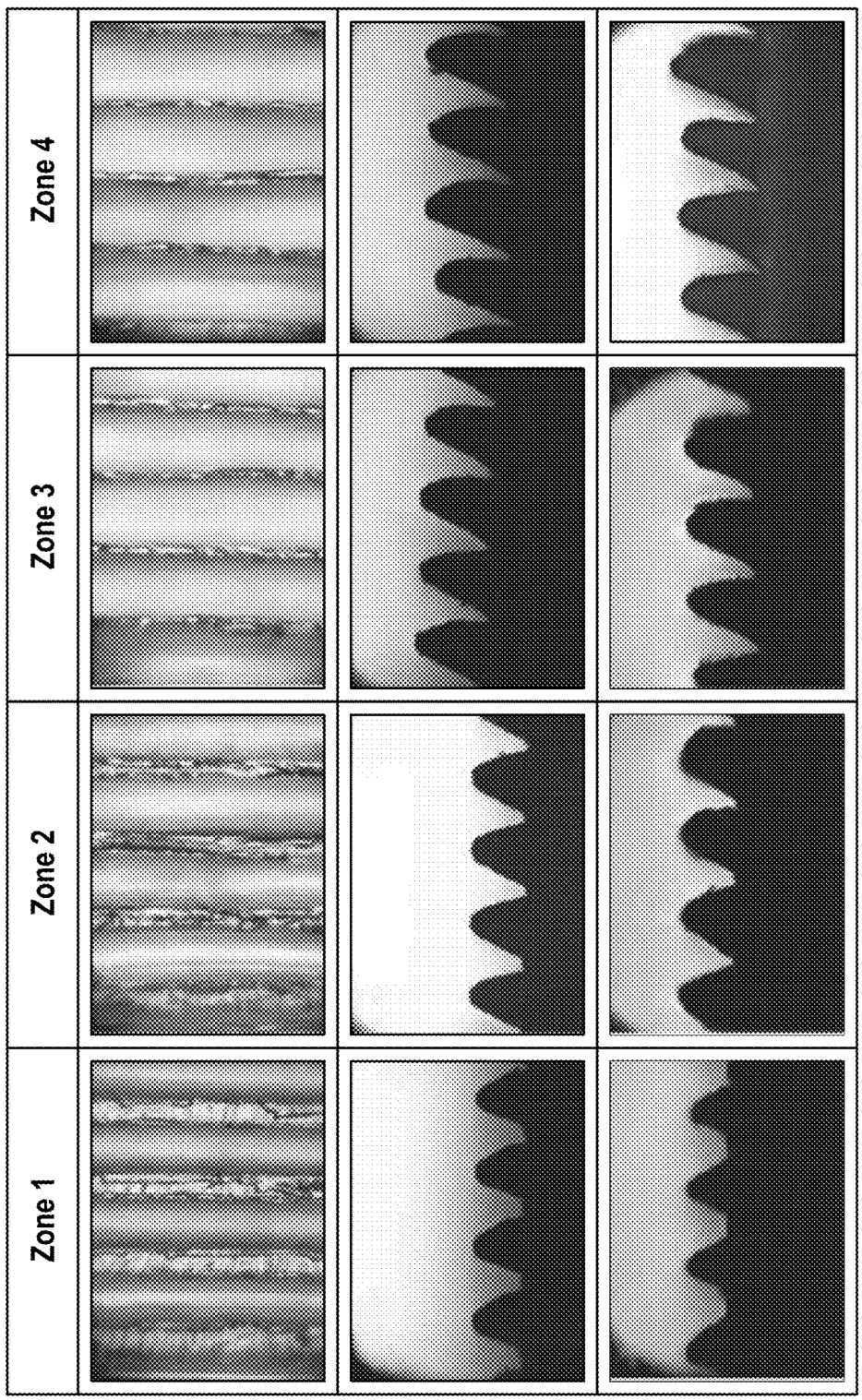
FIG. 11 illustrates embodiments of cooling structures having different design parameters.

In some embodiments, the cooling structure 1050 may include channels as shown in FIG. 11. The cooling structure 1050 may also include microstructures as described in International Application No. PCT/NZ2013/000113. The channels may run parallel to the x axis or the y-axis or any angle between the x and y axes. The channels may be straight or curved. In some embodiments, the channels can be in the shape of spirals. The channels can reduce gas temperature because of the increase in evaporative cooling. The channels can also increase surface area of the interaction between liquid and respiratory gases. For example, the channels located along the side wall of the humidification chamber 140 can collect liquid through capillary forces which evaporates directly from the side walls. In some embodiments, adding the channels can increase the humidity output by at least 7 mg/L.

Figure 12:
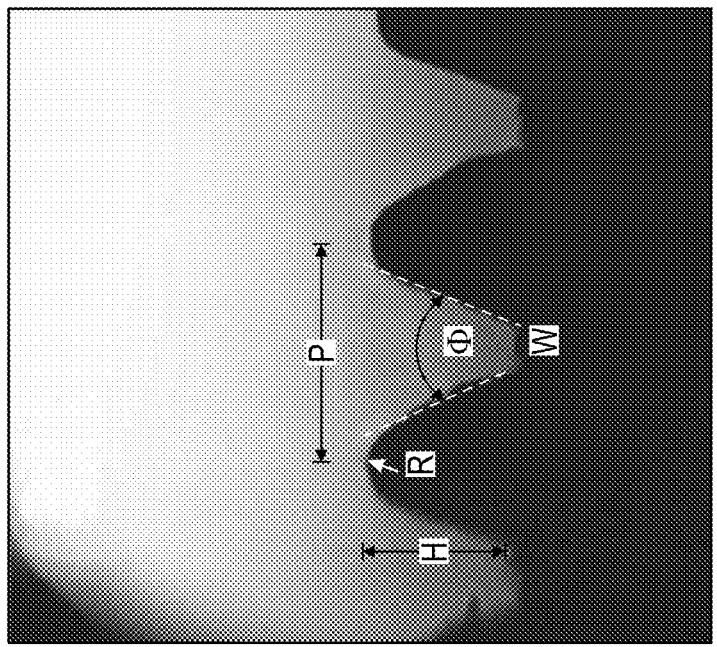
FIG. 12 illustrates the design parameters of the cooling structures shown in FIG. 10.

FIG. 10 illustrates a portion of the channels discussed above. Each zone has different design parameters as illustrated in FIGS. 11 and 12. Modifying the design parameters can change the wetting angle of the surface of the cooling structure 1050. As discussed below, the wetting angle can determine capillary height and also surface forces. In some embodiments, the channels are designed to maximize the wetting angle. Increased wetting can increase capillary height. The channels can also be designed to stop or start capillary filling under certain conditions, such as, at a particular location, or temperature, temperature gradient, or humidity levels. In some embodiments, the design of channels can provide controlled evaporative cooling according to predetermined parameters. Accordingly, the channel parameters may affect evaporation in the humidification chamber 140. In some embodiments, the channel parameters are selected to maximize evaporation. In some embodiments, the $L_f$ parameter is the same as $L_\infty$ in FIG. 14.

In some embodiments, the sidewalls 1060 may also include heating elements on either the interior or exterior of the humidification chamber 140. The cooling structure 1050 may also include heating elements. The heating elements of the sidewall can increase evaporative rate of the liquid adhering to the cooling structure 1050. Further, In some embodiments, the heater plate 240 can be designed to directly heat the chamber walls. For example, the back of the heater plate 240 can be arranged to directly contact the chamber walls and heat the chamber walls directly. The heater plate 240 can also have a diameter larger than the cooling structure 1050. Thus, there may be a gap between the cooling structure 1050 and the sidewall 1060. Accordingly, the heat from the heater plate 240 can be trapped behind the sidewall and the cooling structure 1050 and heat the cooling structure 1050.

In some embodiments, the cooling structure 1050 is manufactured using injection moulding. The materials can be polycarbonate, Arnitel VT3108, PP+Techsurf or any other thermoplastics. The materials can also affect contact angle or the wetting of the liquid on the cooling structure 1050 as shown in FIG. 13. For a polycarbonate material, the contact angle for water can be higher than a material like Arnitel. The contact angle can determine wettability of the material. In some embodiments, higher wettability may be desired to increase capillary height.

Figure 14:
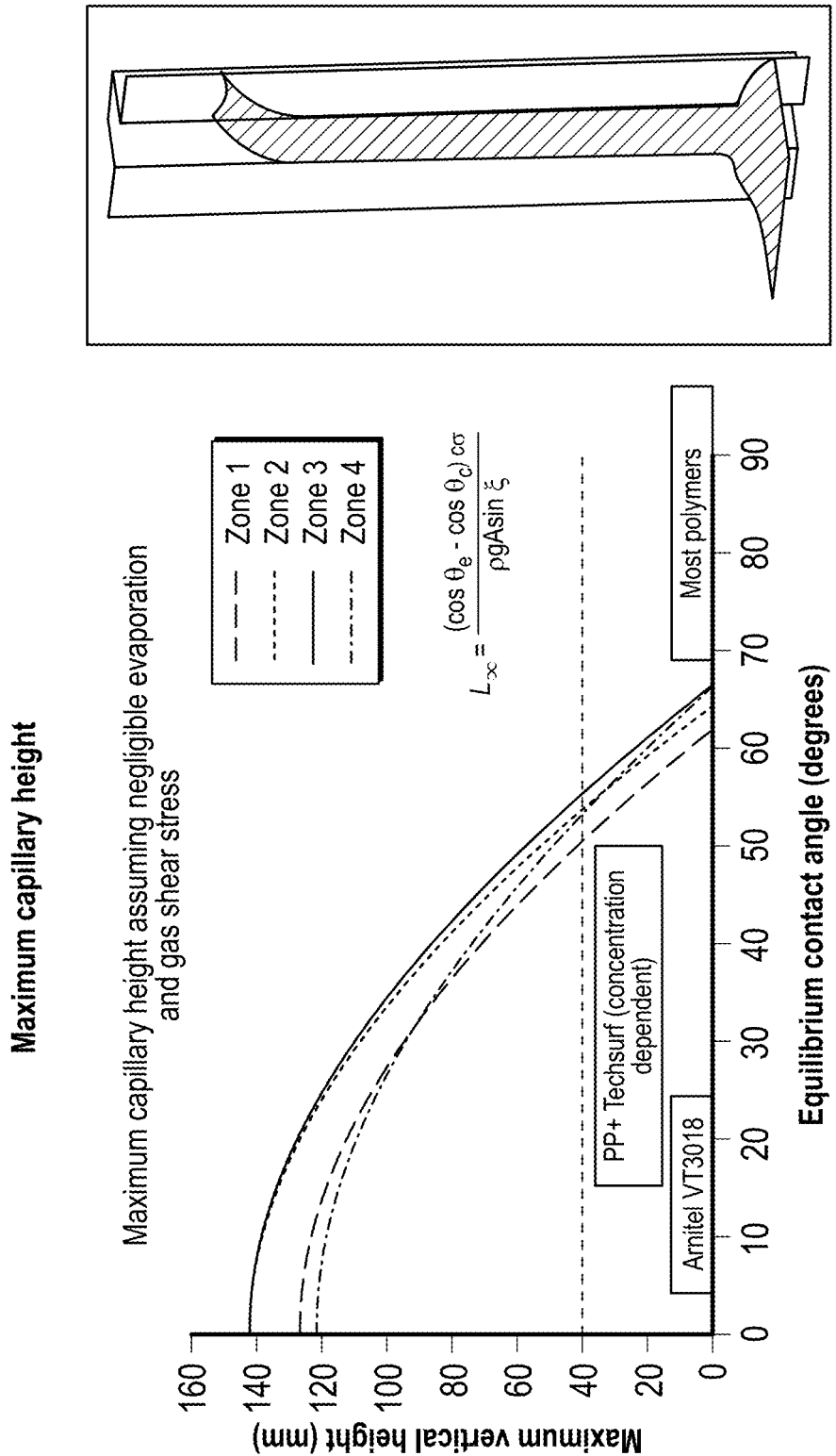
FIG. 14 illustrates capillary height measurements for the cooling structures of FIG. 10.

FIG. 14 illustrates example calculations of capillary heights as a function of design parameters and materials of the cooling structure 1050 shown in FIG. 11. Larger capillary height can indicate that a column of liquid will rise higher along the channels of the cooling structure 1050. When the liquid rises higher, the surface area of the liquid available for evaporative cooling can also increase. As discussed above, evaporative cooling can decrease temperature of the respiratory gases in the humidification chamber. In some embodiments, for the equation shown in FIG. 14, c is the wetted x-sectional length of the channel, A is the cross-sectional area, σ is liquid/vapour surface tension, ρ is liquid density, ξ is inclination of channel (which is 90 deg if vertical) and g is gravity constant.

Figure 15:
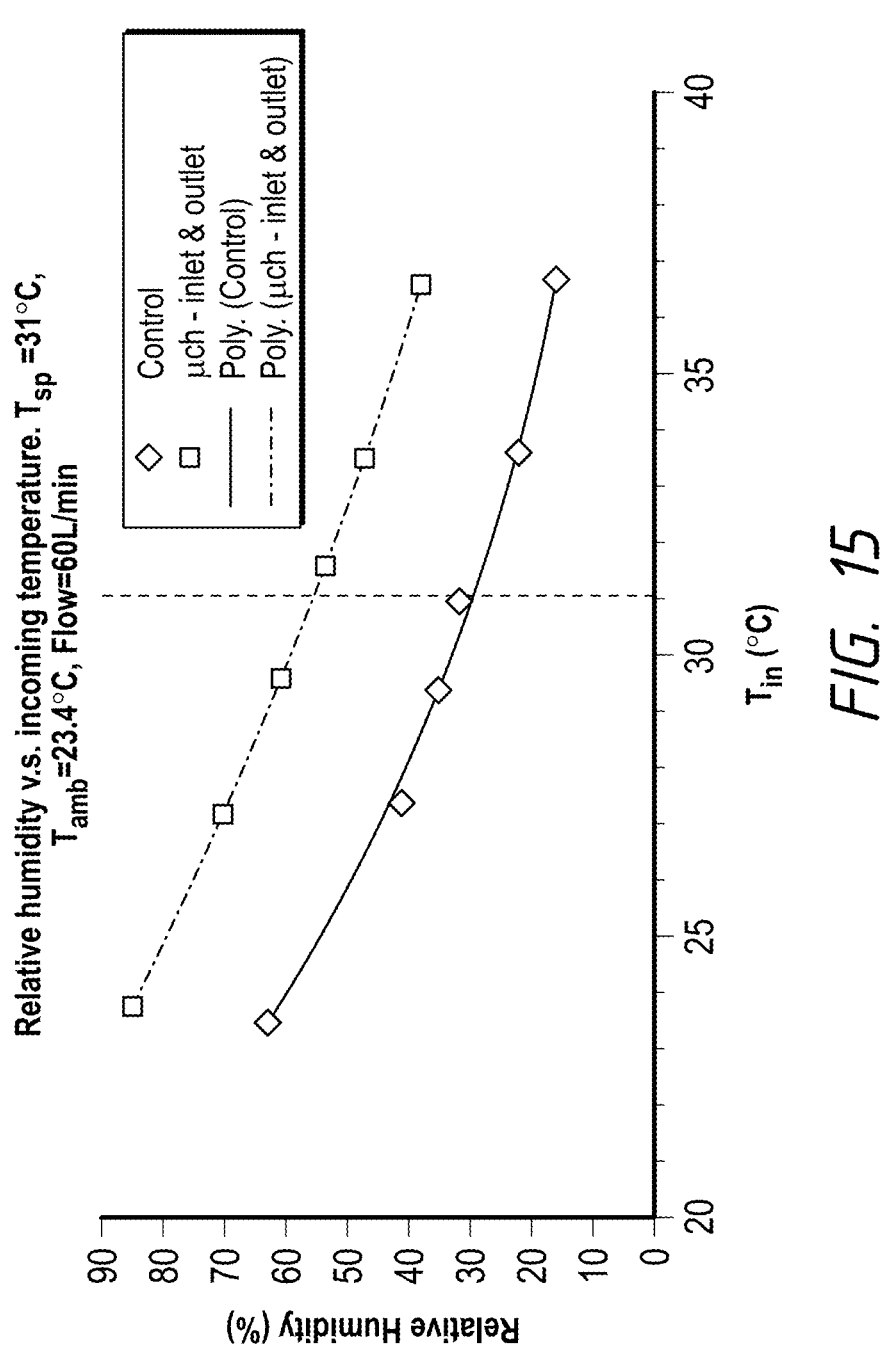
FIG. 15 shows example results corresponding to the change in relative humidity from adding cooling structures to the humidification chamber.

FIG. 15 illustrates results from one of the embodiments described above with the cooling structure 1050 having channels attached to sidewalls near the inlet port 142 and the outlet port 144. The figure shows that the cooling structure 1050 including channels placed inside the humidification chamber 140 can increase the relative humidity added to the respiratory gases.

Figure 16:
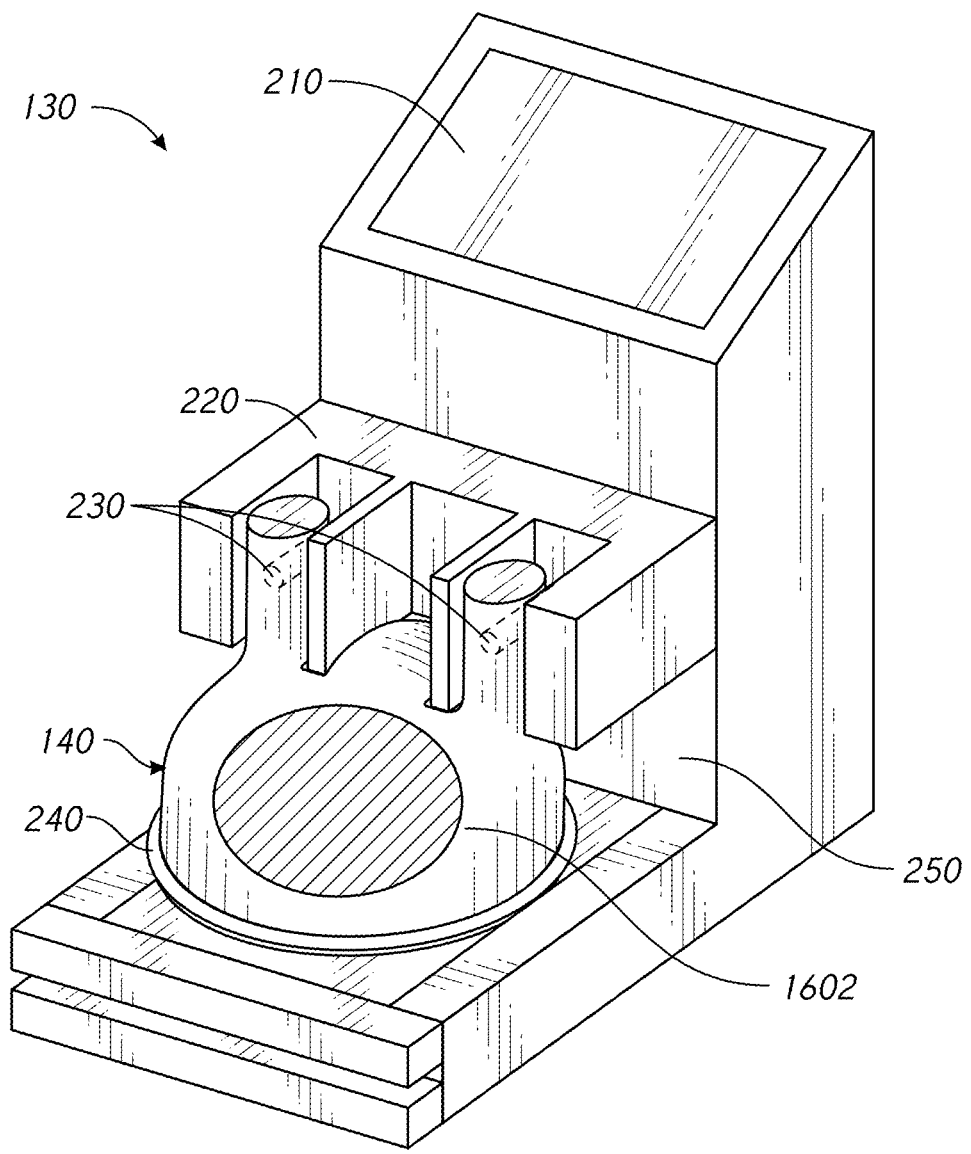
FIG. 16 illustrates an embodiment of a base structure that can be used with the humidification chamber.
Figure 17:
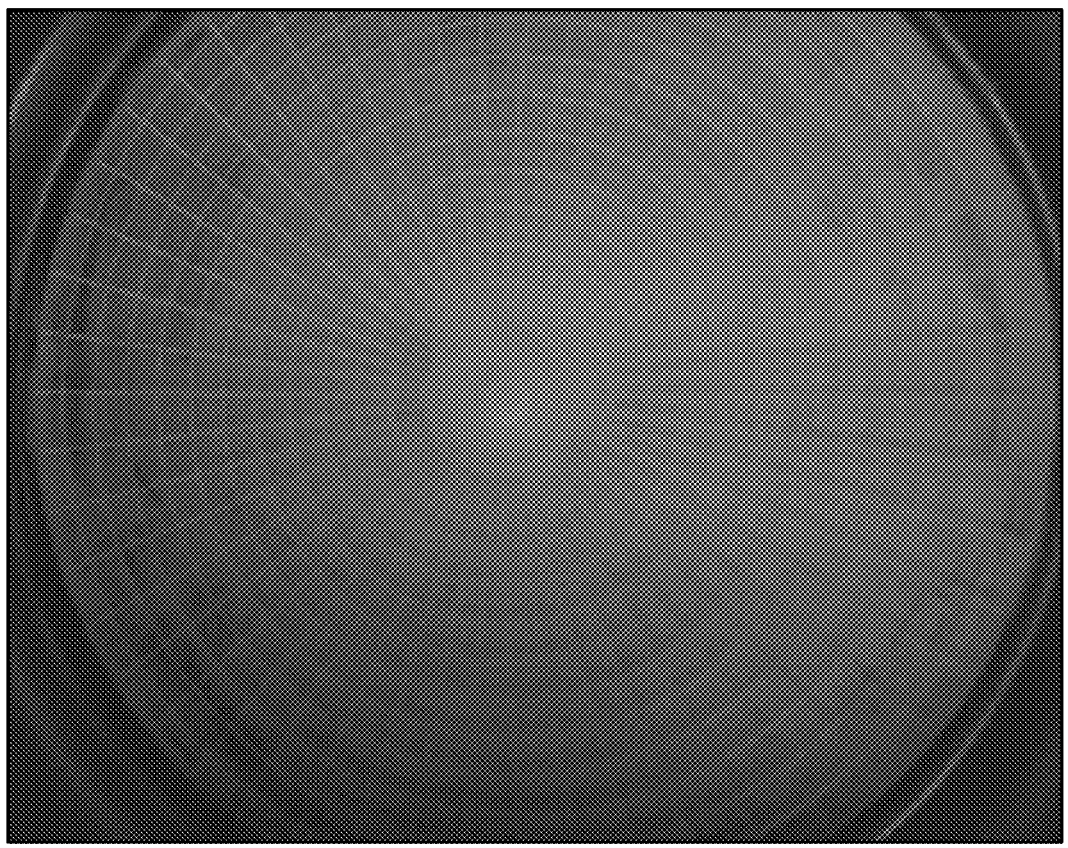
FIG. 17 illustrates a top view of the base structure of FIG. 16.

FIG. 16 illustrates an embodiment of the humidification chamber 140 with a base structure 1602 placed on the base of the humidification chamber 140. In some embodiments, the base structure 1602 can be integral of the base of the chamber. The base structure 1602 can also be removably inserted in the humidification chamber 140. The base structure 1602 can cover some or the entire portion of the base of the humidification chamber 140. In some embodiments, the base structure 1602 lies above the heater plate 240. The base structure 1602 can be designed to hold a thin layer of liquid. An embodiment of the base structure 1602 is shown in FIG. 17. A thin layer of liquid may evaporate faster than a larger volume of liquid. The thin layer of liquid can be continuously maintained using a source (not shown). The base structure 1602 can include channels as discussed above as shown in FIG. 17. Liquid can be fed from a source and directed towards the channels. The design of the channels can increase evaporation. For example, the height of the channel or any other dimension may vary along the length of the channel to account for variations in the base temperature or gas conditions to prevent thin-film break-up (dry out) and maintain high evaporation rates. In some embodiments, the wall tilt is adjusted to maximize fluid recirculation (thus temperature homogenization) via surface tension (Marangoni) driven convection.

In some embodiments, the controller 132 can automatically adjust the set point based on detecting the temperature of the respiratory gases at the inlet port 142. The controller 132 can also track humidity and/or flow rate of the respiratory gases at the inlet port 142. In some embodiments, the controller 132 can receive a humidity indication based on a user input. In some embodiments, the controller 132 can receive humidity measurements from a humidity sensor.

The controller 132 can measure a difference between the inlet gas temperature and the set point. If the temperature difference is small, the controller 132 can automatically increase the set point temperature. This can enable the heater plate 240 to run longer and add sufficient humidity to the respiratory gases. In some instances, if the controller 132 determines that the humidity in the gases at the inlet port 142 is not that different from the set point humidity, the controller 132 may not change the temperature set point. The controller 132 can also determine the set point based on the flow rate. For a high flow rate, the controller 132 may increase the temperature set point to increase humidity generation.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A structure configured for use with a humidification system, the structure comprising:
   a base;
   a shroud protruding from a first portion of the base, wherein the shroud is configured to cover a first sensor, wherein the first sensor is configured to protrude from a second portion of the base that is different from the first portion, the first sensor configured to be received into a wall of a removable humidification chamber of the humidification system to determine a characteristic of a gases flow,
   a hood protruding from a third portion of the base that is different from the first and second portions, the hood being configured to facilitate alignment of the removable humidification chamber of the humidification system relative to the structure, the hood defining an opening through the hood such that the opening allows heat to dissipate form the humidification chamber.

2. The structure according to claim 1, wherein the first sensor is configured to measure the temperature of the gases flow.

3. The structure according to claim 1, wherein the first sensor is configured to protrude into an outlet port of the removable humidification chamber of the humidification system.

4. The structure according to claim 1, wherein the structure comprises a post configured to support a second sensor.

5. The structure as claimed in claim 4, wherein the second sensor is configured to protrude into an inlet port of the removable humidification chamber of the humidification system.

6. The structure according to claim 1, wherein the shroud facilitates pneumatic coupling between the removable humidification chamber and an inspiratory tube.

7. The structure according to claim 1, wherein the shroud is configured to form an electrical connection with an inspiratory tube.

8. The structure according to claim 7, further comprising electrical contacts that form the electrical connection with the inspiratory tube.

9. The structure according to claim 8, wherein the shroud is configured to cover the electrical contacts.

10. The structure according to claim 1, further comprising a second sensor and a third sensor at a first end, wherein the first sensor is at a second end.

11. The structure according to claim 1, wherein the structure is shaped such that the hood is the only portion of the structure that is configured to contact the humidification chamber, thereby improving heat dissipation.

12. The structure according to claim 1, wherein the opening reduces a mechanical contact between the humidification chamber and the structure.

13. The structure according to claim 1, wherein the opening is greater than or equal to 50% of a surface area of the hood.

* * * * *

UNITED STATES PATENT AND TRADEMARK OFFICE
CERTIFICATE OF CORRECTION

PATENT NO. : 11,278,689 B2
APPLICATION NO. : 15/525257
DATED : March 22, 2022
INVENTOR(S) : Laith Adeeb Hermez et al.

It is certified that error appears in the above-identified patent and that said Letters Patent is hereby corrected as shown below:

In the Claims

At Column 14, Line 22, In Claim 1, delete "form" and insert --from--.

Signed and Sealed this
Sixteenth Day of August, 2022

Katherine Kelly Vidal
*Director of the United States Patent and Trademark Office*